(12) United States Patent
Paterson et al.

(10) Patent No.: US 7,256,256 B1
(45) Date of Patent: Aug. 14, 2007

(54) CDK4 BINDING PEPTIDE

(75) Inventors: Bruce M. Paterson, Bethesda, MD (US); Jian-Min Zhang, Richmond, VA (US)

(73) Assignee: United States of America as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 10/018,964

(22) PCT Filed: May 25, 2000

(86) PCT No.: PCT/US00/14489

§ 371 (c)(1),
(2), (4) Date: Apr. 11, 2002

Related U.S. Application Data

(60) Provisional application No. 60/139,934, filed on Jun. 18, 1999.

(51) Int. Cl.
```
A61K 38/00    (2006.01)
A61K 38/04    (2006.01)
C12P 21/06    (2006.01)
C12P 21/04    (2006.01)
C12P 21/00    (2006.01)
```
(52) U.S. Cl. .................... 530/326; 435/69.1; 435/69.7; 435/71.1; 514/2
(58) Field of Classification Search ................ 530/350; 435/15
See application file for complete search history.

(56) References Cited

OTHER PUBLICATIONS

NCBI Data Base Acc#AAA74374 Deschesne et al. MyoD gene product Aug. 14, 1995.*
Zhang et al. Coupling of the cell cycle and myogenesis through the cyclin D1-dependent interaction of MyoD with cdk4. EMBO J. Feb. 15, 1999;18(4):926-33.*
NCBI DataBase Accession No. AAA74374 MyoD gene product Aug. 14, 1995 from Deschesne et al Mol Cell Biol. Aug. 1994;14(8):5474-5486.*
Witkowski et al, Conversion of a beta-ketoacyl synthase to a malonyl decarboxylase by replacement of the active-site cysteine with glutamine. Biochemistry. Sep. 7, 1999;38(36):11643-11650.*
Wishart et al, A single mutation converts a novel phosphotyrosine binding domain into a dual-specificity phosphatase. J Biol Chem. Nov. 10, 1995;270(45):26782-26785.*
UniProt_03 DataBase Accession No. P15172 Myoblast determinationprotein 1(Myogenic factor 3) (Myf-3) Nov. 1, 1991 from Pearson-White Human MyoD: cDNA and deduced amino acid sequence. Nucleic Acids Res. Mar. 11, 1991; 19(5): 1148.*
Pearson-White et al. Human MyoD: cDNA and deduced amino acid sequence. Nucleic Acids Res. Mar. 11, 1991; 19(5): 1148.*
Morgan, D.O. Cyclin-dependent kinases: engines, clocks, and microprocessors. Annu Rev Cell Dev Biol. 1997;13:261-91. Review.*

Zhang, J. et al., "Coupling of the cell cycle and myogenesis through the cyclin D1-dependent interaction of MyoD with cdk4". *The EMBO Journal*, vol. 18, No. 4, pp. 926-933 (1999).
Zhang, J. et al., "Direct inhibition of G₁ cdk kinase activity by MyoD promotes myoblast cell cycle withdrawal and terminal differentiation". *The EMBO Journal*, vol. 18, No. 24. pp. 6983-6993 (1999).
Pan et al., 2001, "A cyclin D1/cyclin-dependent kinase 4 binding site within the C domain of the reinoblastoma protein", *Cancer Res.* 61: 2885-2891.
Zhang et al., 1999, "Evolutionary conservation of MyoD function and differential utilization of E proteins," *Dev. Biol.* 208: 465-472.
NCBI GenBank Accession No. AAC39521, GI:17986211 for human CDK4.
NCBI GenBank Accession No. NP_ 034000, GI6753380 for mouse CDK4.
NCBI DataBase Accession No. U12574; GI:632486 for Sus acrofa myogenic regulatory factor MyoD (myoD) gene, complete cds, dated Feb. 10, 1996.
NCBI DataBase Accession No. X56677: GI:34861 for Human MyoD mRNA, dated Apr. 18, 2005.
NCBI DataBase Accession No. S64244; GI:236945 for cfla+POU Domain, dated May 7, 1993.
NCBI DataBase Accession No. D90157; GI:222836 for gallus gallus mRNA for myogenin, dated Dec. 17, 2002.
NCBI Database Accession No. L34006; GI:504490 for chicken (clone CMD1) MyoD gene, promoter and complete cds, dated Aug. 17, 1995.
NCBI DataBase Accession No. M31116; GI:214587 for X.laevis MyoD1 homologue (mfl) gene (expressed prior to somite formation) mRNA, complete cds, dated Apr. 28, 1993.
NCBI DataBase Accession No. M84176; GI:205602 for Rattus norvegicus myogenic regulatory factor (MyoD) gene, complete cds, dated Apr. 27, 1993.
NCBI DataBase Accession No. X16106; GI:64906 for Xenopus laevis myoD gene for myc-related DNA-binding protein, dated Apr. 18, 2005.
NCBI DataBase Accession No. X16189; GI:62868 for Chicken CMD1 mRNA for mouse MyoD1 homologue, dated Apr. 18, 2005.
NCBI DataBase Accession No. AF027148; GI:3403164 for *Homo sapiens* myogenic determining factor 3 (MYOD1) gene, complete cds, dated Aug. 7, 1998.

(Continued)

*Primary Examiner*—Sheridan Swope
(74) *Attorney, Agent, or Firm*—Merchant & Gould P.C.

(57) ABSTRACT

The invention provides a CDK4 binding peptide, and a nucleic acid sequence coding therefore, that is capable of specifically binding cyclin dependent kinase (CDK4) to inhibit CDK4 activity and cell growth. The invention also includes variants of the CDK4 binding peptide which comprise polypeptides which have at least about 80% amino acid sequence identity with the amino acid sequence of the CDK4 binding peptide. In another embodiment, the invention provides chimeric molecules comprising a CDK4 binding peptide fused to a heterologous peptide or amino acid sequence, preferably a nuclear localization signal. Therapeutic and diagnostic methods are also provided.

5 Claims, 14 Drawing Sheets

OTHER PUBLICATIONS

Chang et al., "Cloning and *in vivo* expression of the pig MyoD gene", *J. Muscle Res. Cell. Motil.*, 16(3), 243-247 (1995).

Chen et al., "Methylation Alterations of the *MyoD1* Upstream Region Are Predictive of Subclassification of Human Rhabdomyosarcomas", *Am. J. Pathol.*, 152(4):1071-1079 (1998).

Crescenzi et al., "MyoD induces growth arrest independent of differentiation in normal and transformed cells", *Proc. Natl. Acad. Sci. USA*, 87:8442-8446 (1990).

Deschesne et al., "E-Box- and MEF-2-Independent Muscle-Specific Expression, Positive Autoregulatin, and Cross-Activation of the Chicken *MyoD* (CMD1) Promotor Reveal an Indirect Regulatory Pathway", *Mol. Cell. Biol.*, 14(8):5474-5486 (1994).

Diehl et al., "Inhibition of cyclin D1 phosphorylation on threonine-286 prevents its rapid degradation via the ubiquintin-proteasome pathway", *Genes Dev.*, 11:957-972 (1997).

Finkel et al., "Detection and Modulation in Vivo of Helix-Loop-Helix Protein- Protein Interactions", *J. Biol. Chem.*, 268:5-8 (1993).

Fujisawa-Sehara et al., "Myogenin Contains Two Domains Conserved Among Myogenic Factors", *Mol. Biol. Chem.*, 265(25):15219-15223 (1990).

Helin et al., "Inhibition of E2F-1 Transactivation by Direct Binding of the Retinoblastoma Protein", *Mol. Cell. Biol.*, 13(10):6501-6508 (1993).

Hopwood et al., "MyoD expression in the forming somites is an early response to mesoderm induction in *Xenopus* embryos", *EMBO J.*, 8(11):3409-3417 (1989).

Kaelin et al., "Identification of Cellular Proteins That Can Interact Specifically with the T/E1A-Binding Region of the Retinoblastoma Gene Product", *Cell*, 64(3):521-532 (1991).

Kato, "Direct binding of cyclin D to the retinoblastoma gene product (pRb) and pRb phosphorylation by the cyclin D-dependent kinase CDK4", *Genes Dev.*, 7(3):331-342 (1993).

Kato et al., "Regulation of Cyclin D-Dependent Kinase 4 (cdk4) by cdk4-Activating Kinase", *Mol. Cell. Biol.*, 14:2713-2721 (1994).

Kaye et al., "A single amino acid substitution results in a retinoblastoma protein defective in phosphorylation and oncoprotein binding", *Proc. Natl. Acad. Sci. USA*, 87:6922-6925 (1990).

Kitagawa et al., "The consensus motif for phosphorylation by cyclin D1-Cdk4 is different from that for phosphorylation by cyclin A/E-Cdk2", *EMBO J.*, 15(24):7060-7069 (1996).

Knudsen et al., "Dual Mechanisms for the Inhibition of E2F Binding to RB by Cyclin-Dependent Kinase-Mediated RB Phosphorylation", *Molecular and Cellular Biology*, 17(10):5771-5783 (1997).

Lin et al., "An avian muscle factor related to MyoD1 activates muscle-specific promotors in nonmuscle cells of different germ-layer origin and in BrdU-treated myoblasts", *Genes Dev.*, 3:986-996 (1989).

Ma et al., "Crystal Structure of MyoD bHLH Domain-DNA Complex: Perspectives on DNA Recognition and Implications for Transcriptional Activation", *Cell*, 77:451-459 (1994).

Munro et al., "A C-Terminal Signal Prevents Secretion of Luminal ER Proteins", *Cell*, 48:899-907 (1987).

Pearson-White et al., "Human MyoD: cDNA and deduced amino acid sequence", *Nucleic Acid Res.*, 19(5):1148 (1991).

Rizutto et al., "Rapid changes of mitochondrial $Ca^{2+}$ revealed by specifically targeted recombinant aequorin", *Nature*, 358:325-327 (1992).

Scales et al., "Two Distinct *Xenopus* Genes with Homology to MyoD1 Are Expressed before Somite Formation in Early Embryogenesis", *Molecular and Cellular Biology*, 10(4):1516-1524 (1990).

Serrano et al., "A new regulatory motif in cell-cycle control causing specific inhibition of cyclin D/CDK4", *Nature*, 366:704-707 (1993).

Shirakata et al., "Dimerization specificity of myogenic helix-loop-helix DNA-binding factors directed by nonconserved hydrophilic residues", *Genes & Developement*, 7:2456-2470 (1993).

Sorrentino, "Cell proliferation inhibition by *MyoD1* independently of myogenic differentiation", *Nature*, 345:813-815 (1990).

Stojanovic et al., "Comparison of five methods for finding conserved sequences in multiple alignments of gene regulatory regions", *Nucleic Acids Research*, 27(19):3899-3910 (1999).

Vaidya et al., "Isolation and structural analysis of the rat *MyoD* gene", *Gene*, 116:223-230 (1992).

Weinberg et al., "Developmental regulation of zebrafish *MyoD* in wild-type, *no tail* and *spadetail* embryos", *Development*, 122:271-280 (1996).

* cited by examiner

Sf-9 Cell Extract (64 ng)

| | Wt | Cyclin D1 | CDK-4 | CDK-4/D1 | CDK-4/D1 |
|---|---|---|---|---|---|
| p16 | | | | | + |

Rb (767-928)

1    2    3    4    5

B

Proteins: 75ng → 300ng

C-Myogenin

CMD

C-terminal CMD

GST-CMD cdk-4BD 1    2    3    4    5

PO4-Rb(Anti-P780)

FIG. 12

| CDK-4 Binding | | CMD aa | No. BrdU+Cells 500 β-gal+Cells (n=6) | % Inhibition |
|---|---|---|---|---|
| + | N-CMD bHLH C-CMD | Vector | 88.4 ± 6.2 | 0% |
| − | N-CMD | 1-299 | 37.1 ± 4.2 | 58% |
| − | bHLH | 1-92 | 86.8 ± 4.8 | 2% |
| + | C-CMD | 93-153 | 58.4 ± 3.9 | 34% |
| | | 153-299 | 46.9 ± 6.4 | 47% |
| − | GST N-CMD | 1-92 | 96.7 ± 5.9 | 0% |
| + | GST | 189-203 | 57.4 ± 4.3 | 41% |

| SPECIES | PEPTIDE SEQUENCE |
|---|---|
| Chicken | YSGPPCSSRRRNSYDS |
| Human | YSGPPSGARRRNCYEG |
| Rat | YSGPPSGPRRQNGYDA |
| Murine | YSGPPSGPRRQNGYDT |
| Pig | YSGPPSGARRRNCYDG |
| | |
| Consensus | YSGPPC/SG/S-RRR/QN-YD/E- |
| | |
| Xenopus-A | YNSPPCGSRRRNSYD |
| Xenopus-B | YNSPPCSSRRRNSYD |
| Zebra fish | FMGPTCQTRRRNSYD |

CDK4 BINDING PEPTIDE

This application is a national stage entry under 35 U.S.C. § 371 of PCT/US00/14489, filed May 25, 2000, which claims the benefit under 35 U.S.C. § 119(e) of U.S. Provisional Patent Application Ser. No. 60/139,934, filed Jun. 18, 1999.

STATEMENT OF RIGHTS TO DISCLOSURES MADE UNDER FEDERALLY SPONSORED RESEARCH AND DEVELOPMENT

The work performed during the development of this disclosure utilized intramural support from the National Institutes of Health. The United States government may have certain rights in the disclosure.

BACKGROUND OF THE INVENTION

The division cycle of eukaryotic cells is regulated by a family of protein kinases known as cyclin-dependent kinases (CDKs). The sequential activation of individual members of this family and their consequent phosphorylation of critical substrates promotes orderly progression through the cell cycle. CDK activities are regulated by cyclin binding, by both positive and negative regulatory phosphorylations and by polypeptide CDK inhibitors. Cellular differentiation is accompanied by the down-regulation of CDK activity, which occurs through at least two mechanisms: down-regulation of cyclin expression which is required for CDK activity; and induction of CDK inhibitor expression. CDK4 is a major catalytic subunit of mammalian D-type cyclins, which act during the $G_1$ phase of the cell cycle to enforce the decision of cells to enter the S phase. The deregulation of eukaryotic CDKs is correlated with many types of cancers.

Three D-type cyclins (D1, D2 and D3) are differentially expressed in proliferating cells in response to various growth factor mediated signals. The D-type cyclins interact combinatorially with CDKs 2, 4, 5 and 6 to form active holoenzymes that facilitate progression through the $G_1$ phase of the cell cycle into S phase. Expression of the D-type cyclins depends on mitogenic stimulation, regardless of the position of the cell in the cycle. Growth factor withdrawal leads to rapid cyclin D destruction, with an associated loss of CDK activity.

A classical example of terminal differentiation is that of skeletal muscle cells. Skeletal muscle differentiation entails the coordination of muscle specific gene expression and terminal withdrawal from the cell cycle. Muscle differentiation is intimately coupled to the cell cycle, such that muscle-specific transcription is initiated only when myoblasts are growth arrested in the $G_1/G_0$ phase.

MyoD is a basic helix-loop-helix (bHLH) protein which plays an important role in the differentiation of skeletal muscle by inducing muscle structural gene expression and cell cycle withdrawal. In particular, MyoD is one of several transcriptional activators of muscle specific gene expression. The mechanisms by which MyoD induces myogenesis involve both the activation of muscle-specific gene expression and withdrawal from the cell cycle. Although proliferating myoblasts express MyoD throughout the cell cycle, the functions of MyoD are repressed in proliferating myoblasts.

Tumor suppressor retinoblastoma protein (RB) suppresses cell proliferation and thus plays an important role in the production and maintenance of the terminally differentiated phenotype of muscle cells. RB also appears to participate in control of entry into the S phase of the cell cycle. Inactivation of RB in terminally differentiated cells allows the cells to reenter the cell cycle. Correspondingly, loss of a functional RB is key step in the development of many human tumors.

The activity of RB is modulated by a phosphorylation/dephosphorylation mechanism during cell proliferation and differentiation. In resting or differentiated cells, RB protein is present in its dephosphorylated from. Underphosphorylated RB inhibits growth promoting transcription factors in the E2F/DP family. In rapidly proliferating cells, RB protein is highly phosphorylated. Maximal phosphorylation is associated with S phase of the cell cycle. Cyclins and CDKs contribute to the sequential phosphorylation of RB to inactivate its growth suppressive function.

SUMMARY OF THE INVENTION

The inventors have identified a peptide (hereinafter referred to as a "CDK4 binding peptide") that is capable of specifically binding a cyclin dependent kinase (CDK4) to inhibit CDK4 activity and cell growth. In one embodiment, the invention provides an isolated nucleic acid sequence comprising DNA encoding the CDK4 binding peptide or a nucleic acid sequence that is complementary to the isolated nucleic acid sequence and remains stably bound to it under at least moderate, and optionally, under high stringency conditions.

In another embodiment, the invention provides an isolated CDK4 binding peptide [SEQ. ID NO: 1]. The invention also includes variants of the CDK4 binding peptide which comprise polypeptides which have at least about 80% amino acid sequence identity with the amino acid sequence of the CDK4 binding peptide.

In another embodiment, the invention provides chimeric molecules comprising a CDK4 binding peptide fused to a heterologous peptide or amino acid sequence, preferably a nuclear localization signal.

Therapeutic and diagnostic methods are also provided.

BRIEF DESCRIPTION OF THE FIGURES

FIG. 11*a* is a photograph of a gel showing that extracts from Sf9 cells coinfected with wild type virus (lane 1), a cyclin D1 encoding virus (lane 2) or a CDK4 encoding virus (lane 3) give background levels of kinase activity on serine 780 (antibody to phosphoserine 780) whereas coinfections with baculovirus stock encoding CDK4 and cyclin D1 produce active CDK4 (lane 4) that specifically phosphorylates RB (GST RB (aa 767–928)) on serine 780. This phosphorylation is inhibited to background levels by the CDK specific kinase inhibitor p16 (lane 5, added as GST-p16).

FIG. 11*b* is a photograph of a gel showing that full sized MyoD(CMD1) (second row), the C-terminus of MyoD (CMD1) (third row) and the fifteen amino acid CDK4 binding domain of MyoD fused to GST (fourth row) inhibit the CDK4-dependent phosphorylation of RB(GST-RB) in vitro whereas myogenin (first row) has no inhibitory affect).

FIG. 12 is a table showing the growth inhibitory effects of the various MyoD(CMD1) subdomains joined to either the pcDNA3 or GST-pCEFL vectors. The number of BrdU positive cells per 500 lacZ positive cells, normalized to vector and averaged for six independent assays is shown. In the top panel, constructs were expressed the pcDNA3 vector. In the lower panel constructs were fused to eukaryotic expression vector, GST-pCEFL, and contained a nuclear localization signal.

FIG. 13 is a photograph of a gel showing the inhibition of RB phosphorylation in C2C12 myoblasts by MyoD(CMD1) and the C-terminus containing the fifteen amino acid CDK4 binding peptide.

FIG. 14 is a sequence comparison of the fifteen amino acid CDK4 binding peptide in chicken MyoD(CMD1) versus human, rat, mouse, pig, xenopus and zebra fish. The consensus is given between chicken and mammals.

DETAILED DESCRIPTION

Definitions

Figure 1:
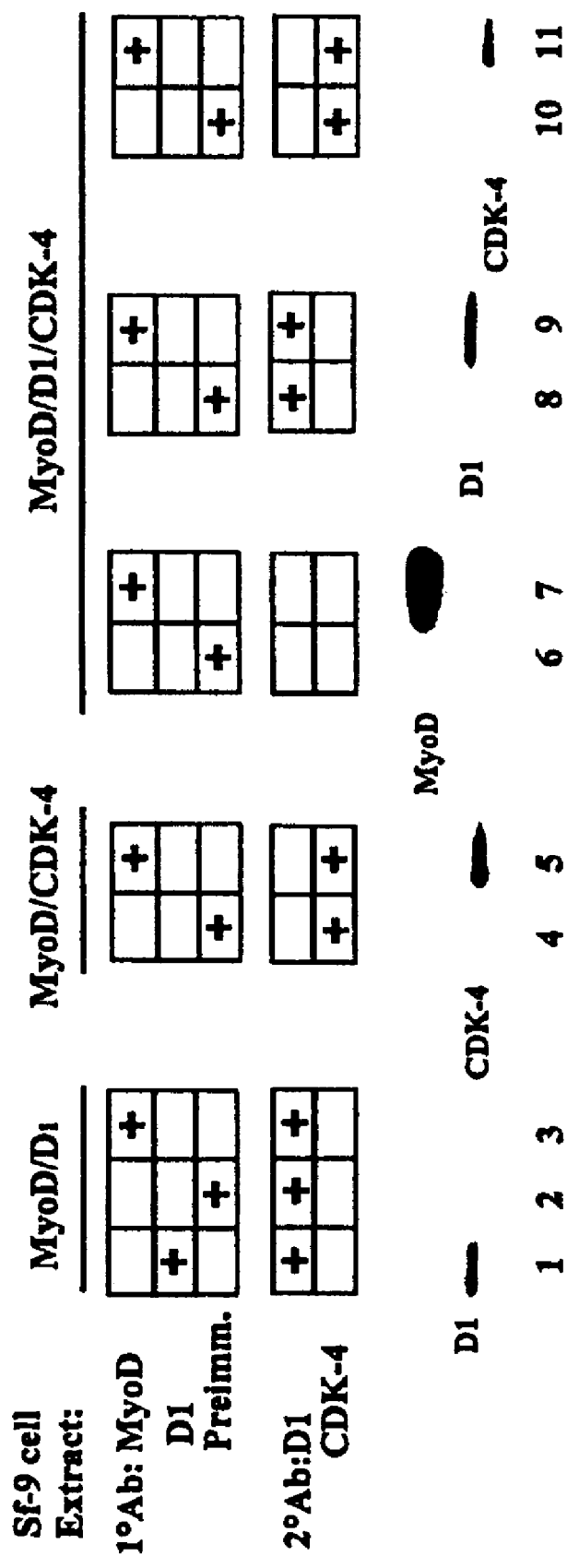
FIG. 1 is a photograph of a gel showing that MyoD binding to CDK4 does not depend upon cyclin D1.

The term "CDK4 binding peptide", when used herein, encompasses both the native sequence shown and variants thereof (which are further defined herein). The CDK4 binding peptide may be isolated from a variety of sources, such as vertebrate sources, including human tissue types, or from another source, or prepared by recombinant or synthetic methods.

A "native" CDK4 binding peptide sequence comprises a polypeptide having the same amino acid sequence as a CDK4 binding peptide derived from nature. Native sequences can be isolated from nature or can be produced by recombinant or synthetic means.

A "variant" of the CDK4 binding peptide includes peptide sequences having at least about 80% amino acid sequence identity with the CDK4 binding peptide shown in [SEQ. ID NO: 1], more preferably about 90%, even more preferably about 95% sequence identity.

"Percent (%) amino acid sequence identity" with respect to the CDK4 binding peptide sequence is defined as the percentage of amino acid residues in a candidate sequence that are identical to the amino acid residues in the CDK4 binding peptide sequence, after aligning the sequences and introducing gaps, if necessary to introduce maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared.

"Percent (%) nucleic acid sequence identity" with respect to the nucleic acid sequences encoding the CDK4 binding peptide is defined as the percentage of nucleotides in a candidate sequence that are identical to the nucleotides in the nucleic acid sequence encoding the CDK4 binding peptide after aligning the sequences and introducing gaps, if necessary, to achieve the maximum percent sequence identity. Alignment for the purpose of determining percent nucleic acid sequence identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared.

"Isolated" when used to describe the peptides disclosed herein, means a polypeptide that has been identified and separated and/or recovered from a component of its natural environment. Contaminant components of its natural environment are materials that would typically interfere with diagnostic or therapeutic use of the polypeptide, and may include enzymes, hormones, and other proteinaceous or non-proteinaceous solutes. In preferred embodiments, the polypeptide is purified (1) to a degree sufficient to obtain at least 15 residues of N-terminal or internal amino acid sequence by use of a spinning cup sequenator, or (2) to homogeneity by SDS-PGGE under non-reducing or reducing conditions using Coomassie blue or, preferably, silver stain. Isolated polypeptide includes polypeptide in situ within recombinant cells, since at least one component of the CDK4 binding peptide natural environment will not be present. Ordinarily, however, isolated polypeptide is prepared by at least one purification step.

An "isolated" nucleic acid molecule is a nucleic acid molecule that is identified and separated from at least one contaminant nucleic acid molecule with which it is ordinarily associated. An isolated nucleic acid molecule is other than in the form or setting in which it is found in nature. However, an isolated nucleic acid molecule includes nucleic acid molecules contains in cells that ordinarily express the protein encoded by that nucleic acid molecule where, for example, the nucleic acid molecule is in a chromosomal location different from that found in nature.

The term "control sequence" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a Nuclear Localization Signal is operably linked to DNA encoding the CDK4 binding peptide if the expressed protein is localized in the nucleus thereby; a promoter or enhancer is operably linked to a coding sequence if it affects the transcription of the sequence. Generally, "operably linked" means that the DNA sequences being linked are contiguous, preferably in the same reading frame. However, enhancers do not have to be contiguous. Linking is accomplished by ligation at convenient restriction sites. If such sites do not exist, a synthetic oligonucleotide adaptor or linkers can be used in accordance with conventional practice.

The term "antibody" is used in the broadest sense and specifically covers single anti-CDK4 binding peptide monoclonal antibodies (including agonist, antagonist, and neutralizing or blocking antibodies) and antibody compositions with polyepitopic specificity. The term "monoclonal antibody" as used herein refers to an antibody obtained from a population of substantially homogeneous antibodies, i.e., the individual antibodies comprising the population are identical except for possible naturally occuring mutations that may be present in minor amounts.

"Active" or "activity" for the purposes herein refers to form(s) of the CDK4 binding peptide which retain the biologic activities of native or naturally occurring MyoD having a CDK4 binding domain.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. Particular examples of cancer include osteosarcoma and rhabdomyosarcoma.

The terms "treating", "treatment", and "therapy" as used herein refer to curative therapy, prophylactic therapy and preventative therapy.

Amino acids may be classified according to the polarities of their side chains. An amino acid having a "non-polar side chain" refers to an amino acid having a side chain that is generally hydrophobic and tends to cluster with other hydrophobic molecules when placed in an aqueous environment, such as water. Examples of amino acids having non-polar side chains are glycine, alanine, valine, leucine, isoleucine, methionine, proline, phenylalanine, and tryptophan. An amino acid having an "uncharged polar side chain" refers to an amino acid having a side chain which includes a hydroxyl, amide or thiol group. Examples of amino acids with uncharged polar side chains are serine, threonine, asparagine, glutamine, tyrosine and cysteine. An amino acid having a "charged polar side chain" refers to an amino acid having a side chain that is generally hydrophyllic. Examples of amino acids having charged polar side chains include lysine, arginine, histidine, aspartic acid and glutamic acid. An amino acid having an "uncharged side chain" includes amino acids with both "non-polar side chains" and "uncharged polar side chains." An amino acid having a "polar side chain" includes amino acids with both "uncharged polar side chains" and "charged polar side chains." Other non-standard amino acids may also be classified using this system.

Composition

The invention is directed towards a newly identified and isolated amino acid sequences and a nucleic acid sequence coding therefore. The isolated peptide of the invention is capable of specifically binding cyclin dependent kinase (CDK4), thereby inhibiting the activity of CDK4 and cell growth. The isolated peptide will hereinafter be referred to as a "CDK4 binding peptide." The CDK4 binding peptide of the invention includes the following fifteen amino acid sequence: Tyr-Ser-Gly-Pro-Pro-$Xaa_1$-$Xaa_2$-$Xaa_3$-Arg-Arg-$Xaa_4$-Asn-$Xaa_5$-Tyr-$Xaa_6$ [SEQ. ID NO: 1] wherein $Xaa_1$ is an amino acid having an uncharged polar side chain, including Cys or Ser; $Xaa_2$ is an amino acid having an uncharged side chain, including Ser or Gly; $Xaa_3$ is an amino acid having an uncharged side chain, including Ser, Ala or Pro; $Xaa_4$ is an amino acid having a polar side chain, including Arg or Gln; $Xaa_5$ is an amino acid having an uncharged side chain, including Ser, Cys or Gly; and $Xaa_6$ is an amino acid having a charged polar side chain, including Asp or Glu. Examples of amino acid sequences which correspond to the CDK4 binding peptide of this invention are depicted in FIG. 14.

The invention is also directed towards a nucleic acid sequence encoding the CDK4 binding peptide sequence. The nucleotide sequence which encodes the 15 amino acid CDK4 binding peptide of the claimed invention can be determined from various published nucleotide sequences for MyoD. See, Table 1. For example, (a) the complete nucleotide sequence of human MyoD can be found in GenBank at Accession Number X56677 or EMBL Accession Number AF027148 which correspond to Pearson-White, S. H., "Human MyoD: cDNA and deduced amino acid sequence" *Nucleic Acids Res.* 19(5): 1148 (1991) and Chen, B., et al. "Methylation alterations of the MyoD1 upstream region are predictive of subclassification of human rhabdosarcomas" *Am J. Pathol.* 152(4): 1071–1079 (1998); (b) the nucleotide sequence which encodes chicken MyoD can be found in GenBank at Accession Number X16189 which corresponds to Lin et al., "An avian muscle factor related to MyoD1 activates muscle-specific promoters in nonmuscle cells of different germ-layer origin and in BrdU-treated myoblasts," *Genes Dev.*, 3(7):986–96 (1989); (c) the nucleotide sequence which encodes Zebrafish MyoD can be found in GenBank/ EMBL at Accession Number Z36945 which corresponds to Weinberg, et al. "Development regulation of zebrafish MyoD in wild-type, no tail and spadetail embryos" *Development* 122:2711–280 (1996). It should be noted that the amino acids which correspond to the CDK4 binding peptide for the various organisms provided above are not the same for each.

Applicants also recognize, and include within the scope of their invention, a nucleic acid sequence for the CDK4 binding peptide which contains codons that are modified according to optimal codon frequencies for a particular cellular host. Redundancy in the genetic code permits variation in the gene sequence. In particular, specific codon preferences are recognized for a specific host such that the disclosed sequence can be adapted as preferred for the desired host. For example, rare codons having a frequency of less than about 20% in known sequences of the desired host are preferably replaced with higher frequency codons. A standard textbook on cell biology such as Genes V, Benjamin Lewin ed. Oxford University Press (1994) (see, Chapter 7, page 172, FIG. 7.9) can be consulted for information on the degeneracy of the genetic code and to provide information regarding the various nucleic acid codons and to which amino acid they correspond.

TABLE 1

| Source/Species | GenBank/EMBL Accession No. | Journal |
|---|---|---|
| Chicken | L34006 | Dechesne, C. A., et al. "E-box and MEF-2 independent muscle-specific expression, positive autoregulation, and cross-activation of the chicken MyoD (CMD1) promoter reveal an indirect regulatory pathway" Mol. Cell. Biol. 14(8): 5474–86 (1994) |
| Human | X5667; AF027148 (EMBL) | Pearson-White, S. H., "Human MyoD: cDNA and deduced amino acid sequence" Nucleic Acids Res. 19(5): 1148 (1991); Chen, B., et al. "Methylation alterations of the MyoD1 upstream region are predictive of subclassification of human rhabdosarcomas" Am J. Pathol. 152(4): 1071–1079 (1998). |
| Rat | M84176 (EMBL) | Vaida, T. B., et al. "Isolation and structural analysis of the Rat MyoD gene" Gene 116: 223–230 (1992) |
| Murine | M18779; M84918; | Davis, R. L., et al "Expression of a single transfected cDNA converts fibroblasts to myoblasts" Cell 51: 987–1000 (1987); Pinney, D. F., et al. "Myogenic lineage determination and differentiation: Evidence for a regulatory gene pathway" Cell 53: 781–93 (1988) |
| Pig | U12574 | Chang, K. C., et al. "Cloning and in vivo expression of the pig MyoD gene" J. Muscle Res. Cell. Motil. 16(3): 243–47 (1995). |
| Xenopus-A | X16106/M31116 | Hopwood, N. D., et al. "MyoD expression in the forming somites is an early response to mesoderm induction in Xenopus embryos" EMBO J. 8(11): 3409–17 (1989); Scales, J. B., et al. "Two distinct Xenopus genes with homology to MyoD1 are expressed before somite formation in early embryogenesis" Mol. Cell. Biol. 10: 1516–1524 (1990); and |
| Zebrafish | Z36945 | Weinberg, et al. "Developmental regulation of zebrafish MyoD in wild-type, no tail and spadetail embryos" Development 122: 2711–280 (1996). |

The peptide of the invention is an amino acid domain from the carboxyterminal region of muscle specific transcription factor (MyoD) which includes the CDK4 binding domain. The CDK4 binding peptide sequence of the invention is well conserved among MyoD proteins of the higher vertebrates (FIG. 14). While not wishing to be bound by theory, the inventors believe that the peptide sequence of the invention specifically binds to CDK4 to inhibit kinase activity. In particular, the inventors believe that interaction inhibits the kinase activity of CDK4 towards retinoblastoma protein (RB). This interaction provides an alternative mechanism that allows MyoD to restrict cell differentiation, independent of a direct interaction with the retinoblastoma protein.

Figure 9:
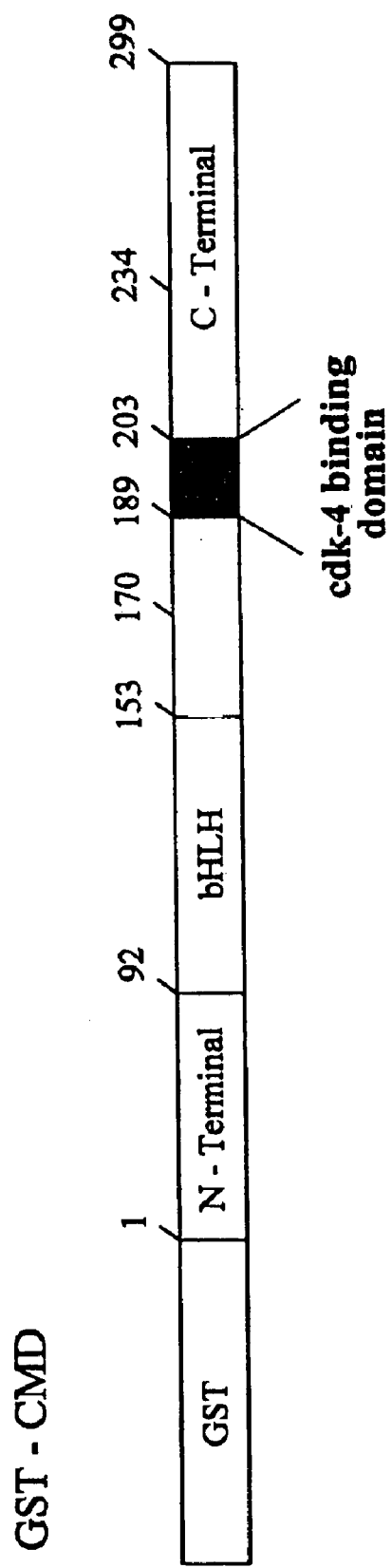
FIG. 9 is a schematic characterization of the CDK-binding domain in MyoD(CMD1) and regions used to study MyoD-CDK4 interactions.

Unlike other vertebrate myogenic factors, the interaction between the peptide of the invention and CDK4 does not involve a highly conserved bHLH domain. Helix-Loop-Helix (HLH) is a motif that is found in a large family of nuclear proteins which appear to play a fundamental role in cellular growth, transcription, and differentiation. The structure, function and location of the bHLH domain is known to those of skill in the art and is published by Ma et al, Cell, 77: 451–459; (1994). Additionally, FIG. 9 provides the amino acid locations of the various domains of chicken MyoD.

In contrast to previous studies that only correlate the bHLH domain of MyoD with growth arrest (Crescenzi et al., PNAS USA, 1990, 87(21):8442–6; and Sorrentino et al., Nature, 1990 345(6278):813–5), the inventors have found that the amino terminus of MyoD exhibits no growth arrest properties, whereas the bHLH domain, and to a greater extent, the carboxy terminus of MyoD both inhibit cell growth. In fact, the inventors have found that the CDK4 binding peptide alone is sufficient to inhibit cell growth and is actually the most efficient growth inhibitory domain in MyoD.

Nuclear Localization Signal

The inventors have also discovered that cyclin D1 regulates MyoD function and the onset of myogenesis by controlling the cellular location of CDK4. In the presence of cyclin D1, CDK4 is translocated from the cytoplasm to nucleus. If it is in sufficient excess to MyoD, nuclear CDK4 sequesters nuclear MyoD and thus inhibits activation of muscle specific genes.

Correspondingly, the inventors have found that the growth inhibitory effect of the CDK4 binding peptide of the invention is enhanced when the peptide further includes nuclear localization signal (NLS) (data not shown). The NLS can be placed anywhere in the protein. For example, the NLS signal can be attached at the amino terminus of the fifteen amino acid MyoD CDK4 binding peptide and fused to GFP. Suitable NLS are described by Fischer-Fantuzzi, et al., Mol. Cell. Biol.; 8: 5494–5503 (1988).

Amino Acid Variants

Covalent modifications of the CDK4 binding peptide are included within the scope of this invention. One type of modification includes deamidation of glutaminyl and asparaginyl residues to the corresponding glutamyl and arpartyl residues, respectively, hydroxylation of proline and lysine, phosphorylation of hydroxyl groups of seryl or threonyl residues, methylation of the α-amino groups of lysine, arginine and histidine side chains, acetylation of the N-terminal amine, and amidation of any C-terminal carboxyl groups. Another covalent modification includes altering the native glycosylation pattern of the polypeptide, for example, by deleting one or more carbohydrate moieties found in the native CDK4 binding peptide and/or adding one or more glycosylation sites that are not present in the native sequence. Another type of covalent modification includes linking the CDK4 binding peptide to one of a variety of non-proteinaceous polymers, e.g., polyethylene glycol, polypropylene glycol, or polyoxyalkylenes.

The CDK4 binding peptide of the invention may also be modified to form a chimeric molecule which includes the CDK4 binding peptide fused to another, heterologous peptide or amino acid sequence. The inventors have found that such fusion proteins can induce growth arrest as efficiently as full-sized MyoD. In one embodiment, the chimeric molecule includes the CDK4 binding peptide fused to a nuclear localization signal. Other examples of heterologous peptide or amino acid sequences include peptides which target the molecule to specific cells, for example, by attachment to an antibody against a surface protein of the target cell. Additionally, the protein can be targeted to various compartments of the cell including the nucleus, the mitochondria (Rizutto et al, Nature; 358: 325–327 (1992)), and endoplasmic reticulum (Munro et al, Cell; 48: 899–907 (1987)).

Nucleic Acid Variants

Applicants recognize, and include within the scope of their invention, a nucleotide sequence (DNA or RNA) encoding the peptide sequence which contains codons that are modified according to optimal codon frequencies for a particular cellular host.

Redundancy in the genetic code permits variation in the gene sequence encoding the peptide sequence of the invention. In particular, specific codon preferences are recognized for a specific host such that the disclosed sequence can be adapted as preferred for the desired host. For example, rare codons having a frequency of less than about 20% in known sequences of the desired host are preferably replaced with higher frequency codons.

Preparation of CDK4 Binding Peptide

The description below relates primarily to production of CDK4 binding peptide by culturing cells transformed or transfected with a vector containing CDK4 nucleic acid. It is, of course, contemplated that alternative methods, which are well known in the art, may be employed to prepare CDK4 binding peptide. For instance, the peptide, or portions thereof, may be produced by direct peptide synthesis using solid-phase techniques. In vitro protein synthesis may be performed using manual techniques or by automation. Automated synthesis may be accomplished, for example, using an Applied Biosystems Peptide Synthesizer (Foster City, Calif.) following the manufacturer's instructions. Various portions of the CDK4 binding peptide may be chemically synthesized separately and combined using chemical or enzymatic methods.

Isolation of DNA Encoding the CDK4 Binding Peptide

DNA encoding the CDK4 Binding Peptide may be obtained from a cDNA library. The library can be screened with probes (such as antibodies to the CDK4 binding peptide or oligonucleotides) designed to identify the gene of interest or the protein encoding by it. Screening the cDNA or genomic library with the selected probe may be conducted using procedures known to those of skill in the art.

Selection and Transformation of Host Cells

Host cells may be transfected or transformed with expression or cloning vectors described herein for production of the CDK4 binding peptide. The host cells are cultured in conventional nutrient media modified as appropriate for inducing promoters, selecting transformants, or amplifying the gene encoding the desired sequences. The culture conditions, such as media, temperature, pH and the like, can be selected by skilled artisans without undue experimentation.

Methods of transfection are known to ordinarily skilled artisans, for example, $CaPO_4$ and electroporation. Alternately, the nucleic acid sequence can be introduced into viable cells using liposomes, microinjection, cell fusion, DEAE-dextran. Depending on the host cell used, transformation is performed using standard techniques appropriate to such cells.

Suitable host cells for cloning or expressing the DNA in the vectors herein include prokaryote, yeast, or higher eukaryotic cells. Suitable prokaryotes include, but are not limited to eubacteria, such as Gram-negative or Gram-positive organisms, for example, Enterobacteriaceae such as *E. Coli*. Eukaryotic cells, including, but not limited to Sf9 cells, 10T1/2 fibroblasts and C2C12 myoblast can also be transfected.

Vectors

The nucleic acid sequence encoding the CDK4 binding peptide may be inserted into a replicable vector for cloning (amplification of the DNA) or for expression. Various vectors are publicly available. The vector may, for example, be in the form of a plasmid, cosmid, viral particle, phage, or, a baculovirus vector. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to skilled artisans.

The CDK4 binding peptide may be produced recombinantly not only directly, but also as a fusion polypeptide which a heterologous polypeptide, for example, a nuclear localization signal.

Expression and cloning vectors typically include a selection gene, also termed a selectable marker. Typical selection genes encoding proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Expression and cloning vectors also typically include a promoter operably linked to the nucleic acid sequence which encodes the CDK4 binding peptide. Promoters recognized by a variety of potential host cells are well known, and include inducible and non-inducible promoters.

Detecting Gene Amplification/Expression

Gene amplification and/or expression may be measured in a sample directly, for example, by conventional Southern blotting, Northern blotting to quantify the transcription of mRNA, dot blotting (DNA analysis), or in situ hybridization using an appropriately labeled probe based on the sequence provided herein. Alternately, gene expression may be measured by immunological methods, such as immunohistochemical staining of cells or tissue sections and assay of cell culture or body fluids, to quantify directly the expression of a gene product. Antibodies useful for immunohistochemical staining and/or assay of sample fluids may be either monoclonal or polyclonal, and may be prepared in any mammal. Conveniently, the antibodies may be prepared against a native sequence of the CDK4 binding peptide or against a synthetic peptide based on the sequences provided herein or against an exogenous sequence fused to the CDK4 binding peptide and encoding a specific antibody epitope.

Purification

CDK4 binding peptide may be recovered from culture medium or from host cell lysates, for example, by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns; and metal chelating columns. Such methods of protein purification are known to those of skill in the art. The purification step selected will depend, for example, on the nature of the production process used.

Uses

Nucleotide sequences (or their complement) encoding the CDK4 binding peptide have various applications in the art of molecular biology, including uses as hybridization probes, in chromosome and gene mapping and in the generation of anti-sense RNA and DNA. Nucleotide sequences encoding the CDK4 binding peptide are also useful for the preparation of CDK4 binding peptide by the recombinant techniques described herein. The nucleic acid sequences are also useful to generate transgenic animals or "knock out" animals which, in turn, are useful in the development and screening of therapeutically useful reagents. A transgenic animal is an animal having cells that contain a transgene, which transgene was introduced into the animal or an ancestor of the animal at a prenatal, or embryonic, stage. A transgene is a DNA which is integrated into the genome of a cell from which a transgenic animal develops.

The CDK4 binding peptide, as disclosed in the present invention, can be employed therapeutically to inhibit cell proliferation, CDK4 kinase activity or to treat solid tumors, particularly those which over-express CDK4.

The CDK4 binding peptide can be used in in vivo or ex vivo gene therapy methods. In gene therapy applications, genes are introduced into cells in order to achieve in vivo synthesis of a therapeutically effective gene product, for example, the replacement of a defective gene. "Gene therapy" includes both conventional gene therapy where a lasting effect is achieved by a single treatment, and in the administration of gene therapeutic agents, which involves the one time or repeated administration of a therapeutically effective DNA or mRNA. Antisense RNAs and DNAs can be used as therapeutic agents for blocking the expression certain genes in vivo.

Methods of transfection are known to ordinarily skilled artisans. The techniques vary depending upon whether the nucleic acid is transferred into cultured cells in vitro or in vivo, in the cells of the intended host. Examples of suitable techniques for introducing the nucleic acid sequence can be into viable include the use of liposomes, microinjection, cell fusion, DEAE-dextran, calcium phosphate precipitation and electroporation. The currently preferred in vivo gene transfer techniques include transfection with viral (typically retroviral) vectors Depending on the host cell used, transformation is performed using standard techniques appropriate to such cells.

The CDK4 binding peptide and variants thereof may be used therapeutically to inhibit the activity of CDK4 and cell growth or cell division. According to the invention, a composition which includes the peptide of the invention is administered to a cell culture or a patient in need of such treatment wherein the composition includes an effective amount of the CDK4 binding peptide of the invention. The inhibition of CDK4 activity and/or cell growth has applications in diseases in which CDK4 is over expressed, for example, cancer. In particular, the CDK4 binding peptide can be administered to treat solid tumors which over-express CDK4, such as rhabdomyosarcoma (RMS) and osteosarcoma.

Pharmaceutical Composition

Another aspect of the invention is directed towards a pharmaceutical composition for inhibiting CDK4 kinase activity, inhibiting cell division, or treating solid tumors which over-express CDK4. The pharmaceutical composition of the invention includes an effective amount of the CDK4 binding peptide of the invention and a pharmaceutically acceptable excipient or carrier. Suitable pharmaceutical carriers are known by those of skill in the art. Typically, an appropriate amount of a pharmaceutically acceptable salt is used in the formulation to render the formulation isotonic. Examples of the carrier include buffers such as saline, Ringer's solution and dextrose solution. The pH of the solution is preferably from about 5 to about 8, and more preferably from about 7.4 to about 7.8. Further carriers include sustained release preparations such as semipermeable matrices of solid hydrophobic polymers, which matrices are in the form of shaped articles, e.g., films, liposomes, or microparticles. It will be apparent to those persons skilled in the art that certain carriers may be more preferable depending upon, for instance, the route of administration and concentration of the CDK4 binding peptide being administered.

Delivery

Various methods of administration of peptides are known to those skilled in the art. Such methods of administration may include, but are not limited to, surface application, oral and parenteral routes, subcutaneous injection, intravenous injection or other pharmaceutical methods of delivery. The peptide can be targeted to specific cells for use in the treatment of cancer. For example, the peptide can be delivered by liposomes, lipophilic tag, injection, viral vectors or fused to a cell specific antibody. Variants too.

Appropriate dosages of the peptides of the invention will depend upon the condition presented by the individual subject. The dosage administered will vary depending upon factors such as the pharmacodynamic characteristics of the particular agent, and its mode and route of administration; age, health and weight of the recipient; nature and extent of symptoms, kind of concurrent treatment, frequency of treatment, and the effect desired. Effective dosages and schedules for administration may be determined empirically, and making such determinations is within the skill in the art.

Anti-CDK4 Binding Peptide Antibodies

The invention further provides anti-CDK4 binding peptide antibodies. Exemplary antibodies include polyclonal, monoclonal, humanized, bispecific and heteroconjugate antibodies.

The anti-CDK4 binding peptide antibodies may include a polyclonal antibody. Method of preparing polyclonal antibodies are known to those skilled in the art. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the CDK4 binding peptide, and variants or fusion proteins thereof.

Alternatively, the anti-CDK4 binding peptide antibodies may be monoclonal antibodies. Monoclonal antibodies may be prepared using hybridoma methods which are known to those of skill in the art. In a hybridoma method, a mouse, hamster, or other appropriate host animal is typically immunized with an immunizing agent to elicit lymphocytes that produce or are capable of producing antibodies that will specifically bind to the immunizing agent. The immunizing agent may include the CDK4 binding peptide, and variants or fusion proteins thereof. Alternately, the lymphocytes may be immunized in vitro. The lymphocytes are then fused with an immortalized cell line using a suitable fusing agent, such as polyethylene glycol, to form a hybridoma cell. The culture medium in which the hybridoma cells are cultured can then be assayed for the presence of monoclonal antibodies directed against the CDK4 binding peptide, for example, by immunoprecipitation or by an in vitro binding assay, such as radioimmunoassay (RIA) or enzyme linked immunoabsorbent assay (ELISA). Such techniques are known in the art.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted to prevent crosslinking. In vitro methods are also suitable for preparing monovalent antibodies. Digestion of antibodies to produce fragments thereof, particularly, Fab fragments, can be accomplished using routine techniques known in the art.

The anti-CDK4 binding peptide antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as a mouse, rat or rabbit having the desired specificity, affinity or capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least on, and typically two, variable domains, win which all or substantially all of the CDR regions correspond to those of a non-human immunoglobulin and all or substantially all of the FR regions are those of a human immunoglobulin consensus sequence. The humanized antibody optimally also comprises at least a portion of an immunoglobulin constant region (Fc), typically that of a human immunoglobulin. Methods for humanizing non-human antibodies are well known in the art.

Bispecific antibodies are monoclonal, preferably human or humanized, antibodies that have binding specificities for at least two different antigens. Heteroconjugate antibodies are composed of two covalently joined antibodies.

The anti-CDK4 binding peptide antibodies of the invention have various utilities. The antibodies can be used in diagnostic assays for CDK4 binding peptide, e.g., detecting its expression in specific cells, tissues serum or tumors. Various diagnostic assay techniques are known in the art and may be used, such as competitive binding assays, direct or indirect sandwich assays and immunoprecipitation assays conducted in either heterogeneous or homogeneous phases. The antibodies used in the diagnostic assays can be labeled with a detectable moiety capable of producing, either directly or indirectly, a detectable signal. For example, the detectable moiety may be a radioisotope (e.g., $^3$H, $^{14}$C, $^{32}$P, $^{35}$S, or $^{125}$I), a fluorescent or chemiluminescent compound (e.g., fluorescein isothiocyanate, rhodamine, or luciferin) or an enzyme (e.g., alkaline phosphatase, beta-galactosidase, or horseradish peroxidase). Any known method for conjugating the antibody to the detectable moiety may be employed.

The antibodies of the invention are also useful for affinity purification of CDK4 binding peptide from recombinant cell culture or natural sources. In this process, the antibodies are immobilized on a suitable support, such as Sephadex resin or filter paper, using methods well known in the art. The immobilized antibody is then contacted with a sample containing CDK4 binding peptide to be purified, and thereafter the support is washed with a suitable solvent that will remove substantially all the material in the sample except the CDK4 binding peptide, which is bound to the immobilized antibody. Finally, the support is washed with another suitable solvent that will release the CDK4 from the antibody. The antibodies also have therapeutic utility.

All references cited in the specification, including in the Working Examples, are hereby incorporated by reference herein.

WORKING EXAMPLES

The following examples are provided to more fully illustrate the principles and practices of the invention. The examples are not intended in any way to limit the scope of the invention.

I. In Vitro Examination of MyoD-CDK4 Interaction

Cloning, Cell Culture and Preparation of Cell Extract

Using primers with the corresponding restriction sites, chicken MyoD, myogenin, and E12 were cloned into EcoR1/Hind3 digested and CIP-treated pM and pVP16 vectors (Clonetech) using standard PCR methods. Sf9 cells were coinfected with baculoviral stocks encoding CDK4 and cyclin to provide a source of activated CDK4 by methods known to those of skill in the art. After incubation for 48 hours at 23° C., cell extracts were prepared from the coinfected Sf9 cells using standard methods in the art.

Binding Assay

The Sf9 cell extract was incubated with agarasoe bound with either glutathione transferase (GST) alone, or GST fusion proteins encoding one of the four different vertebrate myogenic factors from chicken: CMD1 (MyoD), Ch-myogenin, Ch-myf5 an Ch-mrf4 using methods known to those of skill in the art. Any GST complexes formed were recovered on glutathione-Sepharose beads. The recovered GST complexes were then washed, heated in sample buffer and loaded on an SDS-PAGE gel.

Western Blot

The gel was then analyzed by immunoblot with anti-CDK4 affinity purified rabbit polyclonal antibody on HyBond ECL (Amersham). The anti-CKD4 antibody was diluted 1:2,000–5,000. The second antibody was HRP anti-rabbit and was diluted 1:10,000 (Pierce cat. no. 31460). The signal was detected using SuperSignal Ultra Reagent (Pierce cat. no. 34075).

The results indicate that CDK4 binds specifically to GST-MyoD. Only the GST-MyoD bound CDK4 (data not shown). Binding assays performed with extracts from infected Sf9 cells containing only CDK4 or with bacterially produced CDK4 gave the same results (data not shown). Additionally, the ubiquitously expressed bHLH factors E12 and E47 (proteins that form active heterodimers with MyoD) did not bind CDK4 as GST fusion proteins (data not shown). This demonstrates that active kinase is not required for CDK4 to bind specifically to MyoD in vitro. Furthermore, the interaction is not mediated by an unknown protein or proteins in the Sf9 cell extracts since purified bacterial proteins give identical results.

II. In Vivo Determination of MyoD-CDK4 Interaction

Three approaches were used to determine whether or not the observed MyoD-CDK4 interaction occurred in vivo. The combined results from these approaches demonstrate that MyoD and CDK4 interact specifically in vivo.

A. Coimmunoprecipitation

Transfection

Vectors were prepared essentially as described in Example I. Sf9 cells were coinfected to produce either MyoD and CDK4 or MyoD and cyclin D1 protein combinations. After incubating the coinfected Sf9 cells for 48 hours at 23° C., cell extracts were prepared essentially as described in Example 1.

Coimmunoprecipitation

Coimmunoprecipitation reactions were performed sequentially using the Sf9 cell extracts (adjusted for equal protein concentrations in each reaction), under sequential low (no SDS) and high (with SDS) stringency conditions with the antibody combinations shown in FIG. 1 using antibody dilutions of 1:200.

Immunoblotting

Secondary immune complexes were resuspended directly in SDS loading buffer and after SDS-PAGE, proteins were detected by immunoblot essentially as described in Example I, above.

Results

The results are shown in FIG. 1: cells coinfected with baculovirus encoding MyoD and cyclin D1 are in lanes 1 to 3; MyoD and CDK4 are in lanes 4 and 5; and MyoD, CDK4, and cyclin D1 are in lanes 6 to 11. A comparison of lanes 3 and 5 shows that MyoD interacted with CDK4 but not cyclin D1. A comparison of lanes 9 and 11 shows that coexpression of MyoD, CDK4 and cyclin D1 proteins results in MyoD formation of immune complexes containing both CDK4 and cyclin D1. This shows that MyoD binding to the cyclin D1-CDK4 complex does not dissociate the cyclin from the kinase.

MyoD expressed in Sf9 cells is phosphorylated on serine residues, as is MyoD expressed in primary cultures of embryonic chick breast muscle. Because MyoD does not readily form homodimers in vitro unless it is dephosphorylated, MyoD is assumed to bind to CDK4 as a monomer in the immunoprecipitation reactions from Sf9 cell extracts.

Coimmunoprecipitation reactions substituting either virally expressed myf5 or myogenin for MyoD failed to produce immune complexes with CDK4, in agreement with in vitro GST fusion-binding results (data not shown).

B. Mammalian Two-Hybrid System

The interaction between MyoD and CDK4 in vivo was examined using a mammalian version of the yeast two hybrid system described by Finkel et al., (1993) *J Biol Chem* 268, 5–8.

Vector Preparation

MyoD and myogenin (MGN) were each cloned into the gal4 DNA-binding domain vector, pM. CDK4 was inserted into the vp16 activation domain plasmid, pVP16 using methods known to those of skill in the art.

Transfection

10T1/2 fibroblasts ($3 \times 10^5$ cells per 60 mm dish or multiwell plate) grown in DMEM with either 10% fetal calf serum were co-transfected with either gal4-MyoD or gal4-MGN along with vp16-CDK4 and a luciferase reporter using Fugene-6 (Boehringer-Mannheim) according to the manufacturer's directions. 1 µg gal4 luciferase reporter, 2 µg each of the gal4 (pM vector, Clonetech) and vp16 (pvp16 vector, Clonetech) constructs, and 300 ng of the beta galactosidase reporter pCH110 (Pharmacia), a total of 5.3 µg DNA, were used in each transfection. The pSV2-beta galactosidase reporter was used to normalize transfection efficiencies.

After 24–36 hours, if required, cells were placed in 2% horse serum plus insulin (10 µg/ml) to induce differentiation and destabilize cyclin D1. 24–48 hrs later cells were harvested for a luciferase reporter assay.

Luciferase Assay

The gal4 luciferase reporter was constructed by exchanging the CAT cassette from pG5 (Clonetech) for the luciferase cassette in pGL3 (Promega). To do so, pG5 was cut with Eco R1 and flush ended with T4 polymerase. The luciferase gene was digested with BamH1/Hind3, flush ended with T4 polymerase and inserted into pG5. The transfection was performed using Fugene-6 (Boehringer-Mannheim) according to the manufacturer's directions.

24–48 hours after transfection, the luciferase reporter assay was performed according to the manufacturer's directions (Promega, cat. no. E4030) and measured in a Victor 1420 Multilabel Counter. The assay was repeated at least three times with similar results. The luciferase reporter assay was normalized for transfection efficiency with a cotransfected beta galactosidase reporter and by total protein in the cell extract with similar results.

Results

Figure 2:
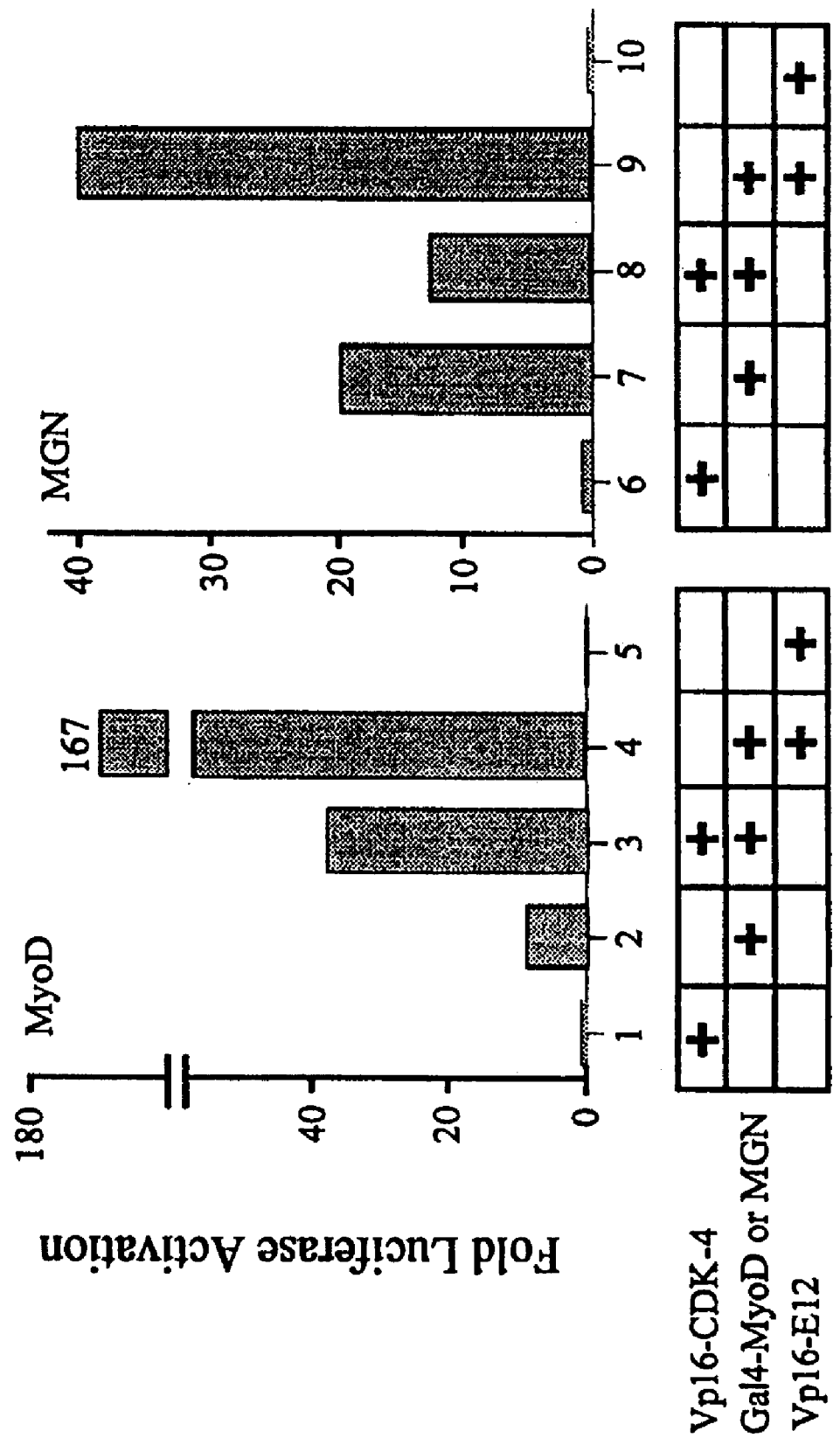
FIG. 2 is a graph showing the in vivo interaction between MyoD and CDK4 in the mammalian two-hybrid system.

MyoD interactions with CDK4 are shown in lanes 1 to 5 and myogenin interactions with CDK4 are shown in lanes 6–10. Gal4 MyoD-vp16 E12 and Gal4 MGN-vp16 E12 interactions (previously established heterodimer partner combinations) were used a positive controls. See, FIG. 2, lanes 1 to 5. Despite the high cellular levels of endogenous CDK4 competing in the two hybrid reaction, a four-fold increase in vp16 CDK4-dependent luciferase reporter activity was routinely detected (an average of three experiments) with the use of the gal4-MyoD construct (FIG. 2, lanes 2 and 3) and not with gal4-MGN (FIG. 2, lanes 7 and 8).

C. Immunoprecipitation

An immunoprecipitation assay was performed to determine whether MyoD and CDK4 interact in dividing C2C12 myoblasts.

Labeling and Preparation of Nuclear Extracts

C2C12 myoblasts were maintained in growth medium and labeled with $^{35}S$ (90 minute labeling) using methods known to those of skill in the art. Nuclear extracts were prepared from $^{35}S$-labeled cultures (90 minute labeling) of C2C12 myoblasts maintained in growth medium.

Coimmunoprecipitation

Figure 3:
FIG. 3 is a gel showing the interaction of MyoD and CDK4 in dividing C2C12 myoblasts.

Nuclear extracts containing equal counts were sequentially coimmunoprecipitated under sequential low (no SDS) and high (with SDS) stringency conditions with indicated primary and secondary antibody combinations shown in FIG. 3 using essentially the same protocol as that described in Example II.

Results

MyoD-CDK4 immune complexes were identified in dividing myoblasts (FIG. 3, lane 6). However, such complexes were not detected in differentiated muscle cultures (data not shown). MyoD and CDK4 interact in dividing C2C12 myoblasts. Lane 6 (FIG. 3) shows that anti-MyoD pulls down CDK4 in dividing myoblasts that can be detected with the secondary CDK4 antibody.

III. Band Shift Assays

To ascertain whether or not CDK4 interferes directly with MyoD transactivation functions, the DNA-binding activity of both MyoD homodimers as well as MyoD-E12 heterodimers was measured in band-shift assays using the bacterially expressed and histidine-tag purified proteins, as described by Shirakata et al., *Genes Dev* 7, 2456–70 (1993).

Cloning and Transfection

His-tagged CDK4 was cloned as the BamH1/Hind3 fragment in the pRSET plasmid (Invitrogen). Chicken MyoD, myogenin, and E12 were cloned into EcoR1/Hind3 digested and CIP-treated pM and pVP16 vectors (Clonetech) using standard PCR methods with primers having the corresponding restriction sites. All constructed clones were checked by sequence analysis on a Perkin-Elmer 310 Genetic Analyzer. His-tagged CDK4 was expressed in the *E. Coli* strain BL21 as described by Shirakata et al., (1993) *Genes Dev.*, 7:2456–70.

Histidine Tag Purification

The protocol for the histidine tag purification technique is identical to Shirakata, supra, with slight changes that are not critical to the outcome.

Renaturation

The his-tagged CDK4 was renatured through sequential dialysis from urea as described by Kato et al., (1994) *Mol. Cell. Biol.* 14:2713–21.

Band Shift Assay

Band shift assays were performed using the bacterially expressed and histidine-tag purified proteins. The MyoD (10 ng), myogenin (10 ng) and E12 (30 ng) proteins from chicken were used with increasing two-fold increments (50–200 ng) of mouse CDK4 protein in the band shift reaction. Limiting amounts of E12 protein were used in the MyoD band shift reactions to observe any CDK4 effects on both the MyoD homodimer as well as the MyoD-E12 heterodimer. DNA binding by a myogenin-E12 heterodimer was used as a control since myogenin does not bind CDK4 in vitro.

Results

Figure 4:
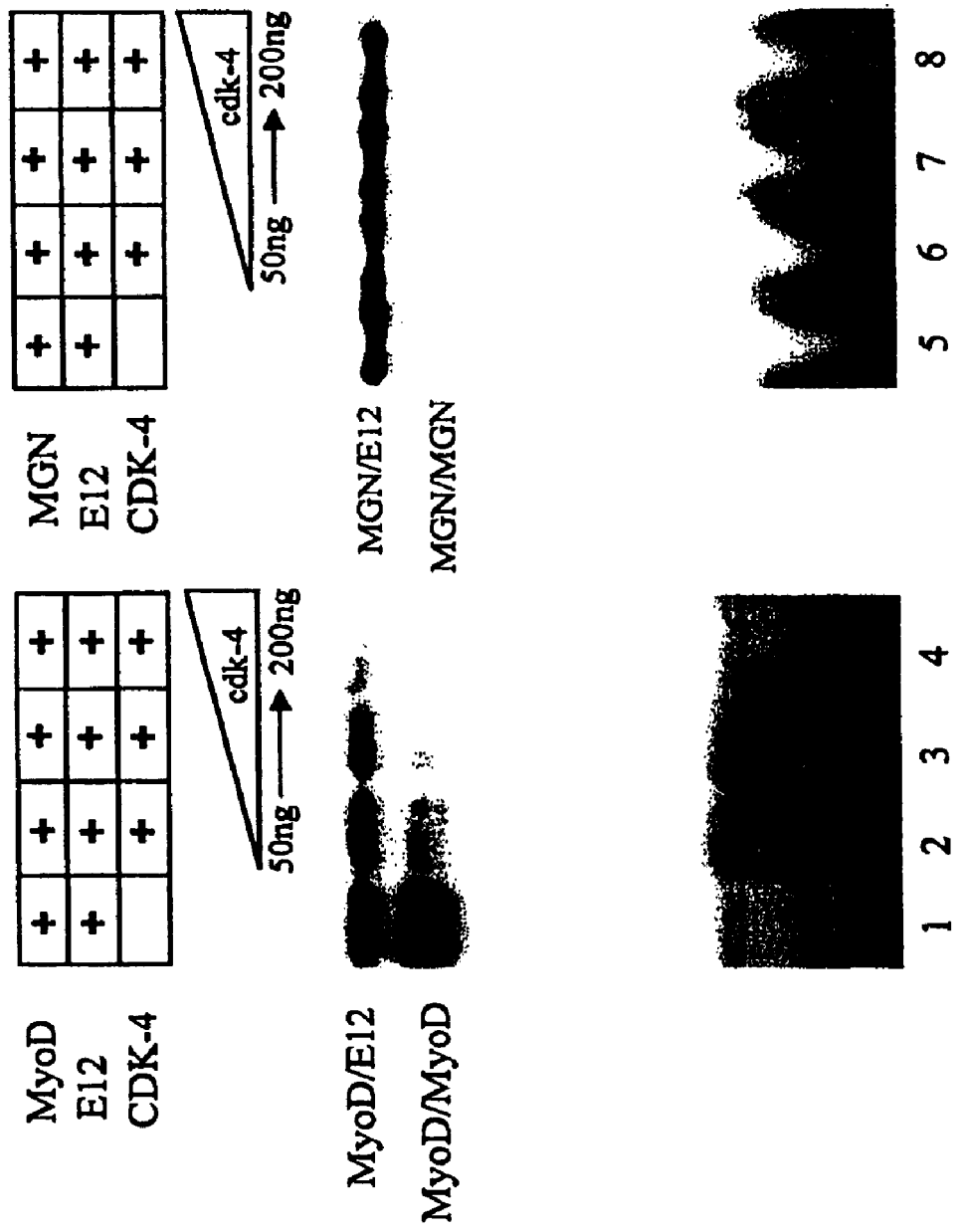
FIG. 4 is a photograph of a gel showing that CDK4 specifically inhibits MyoD-E12 DNA-binding in the absence of cyclin D1.

A CDK4 concentration dependent inhibition of DNA binding was observed with the MyoD homo- and heterodimer complexes (FIG. 4, lanes 1 to 4). Thus, CDK4 protein inhibited DNA-binding by both the MyoD-E 12 heterodimer and the MyoD. No CDK4 inhibition of DNA-binding was observed with the myogenin-E12 complex using the same final level (50–200 ng) of CDK4 protein in the shift reaction (FIG. 4, lanes 5 to 8). Thus, DNA-binding by the myogenin-E12 heterodimer and the myogenin homodimer were unaffected at the equivalent concentrations of CDK4 protein in the binding reaction.

Because the actual amount of properly renatured CDK4 protein is unknown, the effective inhibitory ratio of CDK4 to MyoD-E 12 complex may be significantly less than five-fold. We assume that CDK4 dissociates the DNA-binding complexes, since no evidence for a supershift was noted either with the addition of CDK4 protein or CDK4 antibody to the shift reactions (data not shown). Most importantly, in agreement with the earlier protein binding studies, CDK4 inhibition of DNA-binding by the MyoD-E12 heterodimer did not depend upon cyclin D1 and, therefore, does not require the active kinase. Thus, CDK4 specifically inhibits MyoD-E12 DNA binding in the absence of cyclin D1.

IV. Immunofluorescence

Immunofluorescence assays were used to determine whether CDK4 was differentially located in nuclei during myogenesis and to determine the effect of interactions between MyoD, cyclin D1 and CDK4.

Immunofluorescence

To determine whether CDK4 was differentially localized in nuclei during myogenesis, dividing myoblasts in growth medium (GM) as well as differentiated cultures of C2C12 mouse myoblasts in differentiation medium (DM) were reacted with antibodies to CDK4 and cyclin D1 and examined by immunofluorescence.

The antibodies to CDK4 and cyclinD1 were used at 1:200–500 dilution (rabbit or mouse anti-CDK4 and anti-cyclin D1, Santa Cruz). Second antibody dilutions were also 1:200–500 with either Alexa 488 (green) goat anti-rabbit or mouse, or Alexa 594 (red) goat anti-rabbit or mouse (Molecular Probes).

Results

The results demonstrated that CDK4 is located in the nuclei of dividing myoblasts but translocates to the cytoplasm in differentiated myotubes (data not shown). Furthermore, cyclin D1 is expressed in the nuclei of dividing cells and is completely absent in the nuclei of well differentiated myotubes (data not shown).

V. Ectopic Expression of Cyclin D1

To determine whether or not ectopic expression of cyclin D1 could relocalize and maintain CDK4 in myotube nuclei and, thus, in dividing myoblast nuclei, an ecdysone inducible cyclin D1 construct was transiently transfected into C2C12 myoblasts along with an ecdysone inducible beta galactosidase reporter plasmid.

Because cyclin D1 is rapidly degraded in the absence of growth factors (the conditions used to differentiate muscle cells), a cyclin D1 protein containing an amino acid substitution that renders it resistant to degradation, mutant T286A, was used in place of the wild-type cyclin D1. Mutant T286A contains an alanine for threonine-286 substitution and is described by Diehl et al., (1997) *Genes Dev.*, 11:957–72.

Cloning

Cyclin D1 was amplified from baculovirus stocks with the appropriate primers and was cloned into the PIND vector (Invitrogen) digested with BamH1/EcoR1.

Transfection

C2C12 cells were transfected with 2 μg each of pIND/cyclin-D1(T286A) and pIND/lacZ (Invitrogen). After 24 hours, the cells were switched to differentiation medium (2% horse serum in DMEM with 10 μg/ml insulin).

Induction

Cyclin D1(T286A) was induced by the addition of 1 μM of the ecdysone derivative muristerone. 48 hours later, after well-formed myotubes appeared in the cultures, muristerone was added to a final concentration of 1 μM (Invitrogen).

Immunostaining

Cells were fixed 24 hours post induction and immunostained for CDK4, cyclin D1, and lacZ. The first antibodies were used at 1:200–500 dilution (rabbit or mouse anti-CDK4 and anticyclin D1, Santa Cruz; mouse monoclonal anti-lacZ, Gibco BRL). Second antibody dilutions were also 1:200–500 with either Alexa 488 (green) goat anti-rabbit or mouse, or Alexa 594 (red) goat anti-rabbit or mouse (Molecular Probes) for the immunofluorescent reactions.

Results

The results shown induction of both beta galactosidase and stable cyclin D1 (T286A) in well-formed cotransfected myotubes results in the cytoplasmic to nuclear translocalization of endogenous CDK4 (data not shown). There is essentially no detectable cyclin D1 expression in either myotubes or single cells kept in mitogen depleted differentiation medium (data not shown). In contrast, nuclei of rapidly dividing myoblasts maintained in mitogen rich growth medium have high levels of nuclear cyclin D1 (data not shown).

This result clearly demonstrates that the nuclear localization of CDK4 in C2C12 myoblasts can be regulated by the cellular level of cyclin D1, which, in turn, is dependent upon the levels of mitogens in the growth medium. Neither the addition of growth medium to control myotubes cultures nor the muristerone induction of a wild-type cyclin D1 construct resulted in the nuclear translocation of CDK4 (data not shown). Thus, the kinase triggering the ubiquitination and degradation of wildtype cyclin D1 is likely active in myotubes, regardless of the growth conditions.

VI. Ectopic Expression of CDK4

In this example, the affect of ectopically expressed CDK4 on the transactivation functions of MyoD is Examined.

Plasmid Constructs

Mouse CDK4 was amplified by PCR from baculovirus stocks as outlined in the MaxBac instruction manual (Invitrogen), with primers containing the corresponding restriction sites and was cloned into pVP16 digested with BamH1/Hind3.

Transfection Protocol

10T1/2 fibroblasts ($3 \times 10^5$ cells per 60 mm dish or multiwell plate) grown in DMEM with 10% fetal calf serum (growth medium—conditions which promote the nuclear localization of CDK4) were transfected with cotransfected either with an EMSV MyoD or EMSV myogenin expression plasmid, the MCK CAT reporter plasmid, and either an EMSV CDK4 expression construct or the corresponding empty vector using Fugene-6 (Boehringer-Mannheim) according to the manufacturer's directions.

Results

Figure 5:
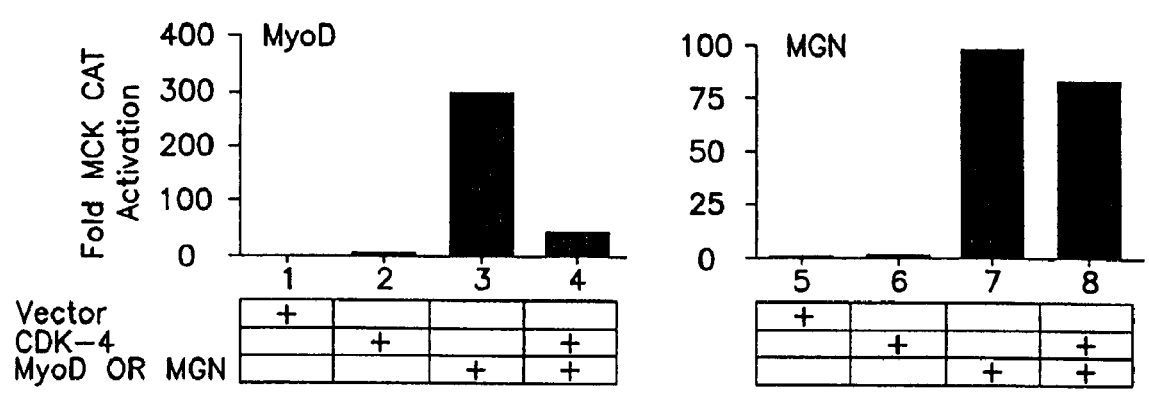
FIG. 5 is a graph showing that CDK4 differentially inhibits MyoD and myogenin activation of the MCK CAT reporter plasmid in 10T1/2 cells grown in differentiation medium (DM).

Ectopic expression of CDK4 selectively inhibits MyoD transactivation functions in growth medium and the MyoD myogenic conversion of 10T1/2 cells in differentiation medium in the absence of cyclin D1. CDK4 differentially inhibits MyoD (FIG. 5, lanes 3 and 4) and myogenin (FIG. 5, lanes 7 and 8) activation of the MCK CAT reporter plasmid in 10T1/2 cells grown in differentiation medium (DM). The ectopic expression of CDK4 was able to significantly suppress the MyoD activation of the MCK-CAT reporter (FIG. 5, lanes 3 and 4). In contrast, little suppression was observed on the myogenin-dependent activation of MCK-CAT (FIG. 5, lanes 7 and 8). Thus, CDK4 significantly disrupts the activation functions of MyoD, while having a minimal effect on myogenin reporter activation.

Inhibition of myogenic differentiation by cyclin D1 thus appears to be a consequence of the cyclin D1-dependent nuclear translocation of CDK4 during myogenesis. Furthermore, CDK4 targeted to the myoblast nucleus in the absence of cyclin D1 blocks myogenesis.

VII. Nuclear Localization of CDK4

This Example examines whether or not CDK4, in the absence of cyclin D1, can inhibit myogenesis.

CDK4 Expression Construct and Transfection

A CDK4 expression construct with a modified with a five-prime nuclear localization signal (NLS) and a three-prime hemagglutinin tag (HA) was prepared. Cultures of 10T1/2 mouse fibroblasts cells were cotransfected as described in Example VI with a fixed amount of pcDNA-MyoD plasmid (1 µg) and increasing amounts of a pcDNA NLSCDK4-HA plasmid (1 to 4 µg). Empty pcDNA vector was used as a control and to balance the total plasmid DNA concentration in the transfection. The percentage of myosin positive cells per MyoD positive cell was scored for a minimum of 300 MyoD positive cells for each plasmid concentration. Cultures were maintained in low mitogen differentiation medium to destabilize and eliminate endogenous cyclin D1 and to induce differentiation of the converted cells.

Results

Figure 6:
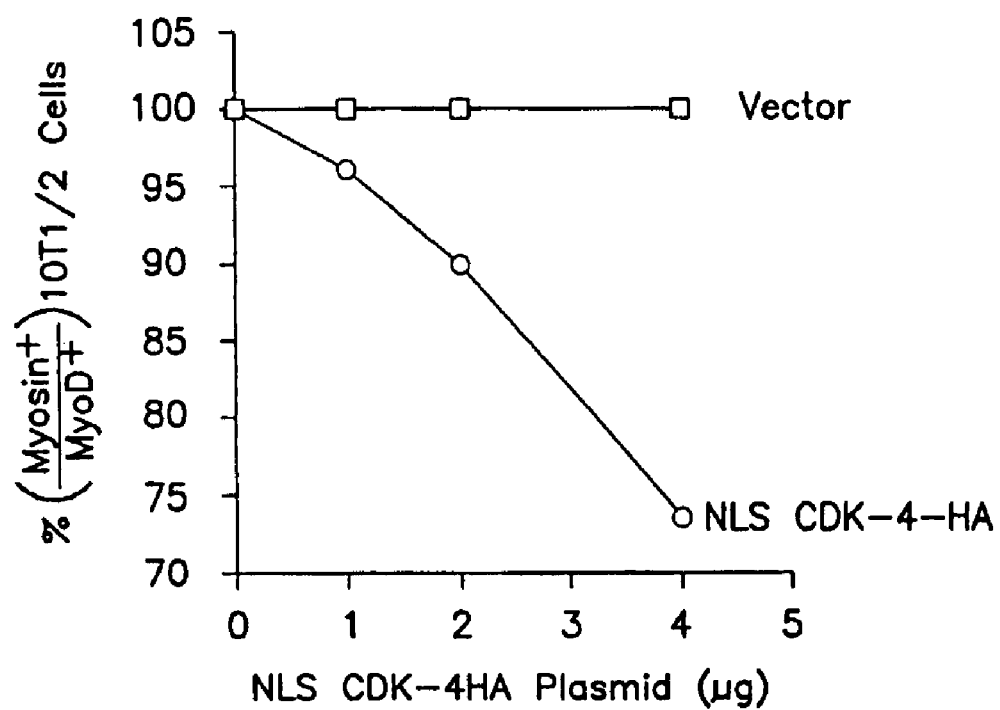
FIG. 6 is a graph showing forced nuclear expression of CDK4 inhibits myogenic conversion of 10T1/2 cells in differentiation medium (DM) in the absence of cyclin D1.

Forced nuclear expression of CDK4 inhibits myogenic conversion of 10T1/2 cells in differentiation medium (DM) in the absence of cyclin D1. Myosin expression in MyoD positive cells was determined as a function of CDK4 plasmid input in the cotransfection. The ratio of myosin positive cells to MyoD positive cells as a function of CDK4 expression plasmid concentration in the transfection was measured. Expression of MyoD and NLSCDK4-HA in the same cell inhibits myogenic conversion (data not shown). MyoD-converted myogenic cells in the absence of NLSCDK4-HA fuse, express MyoD and myosin (data not shown). The forced nuclear localization of CDK4 resulted in an increased number of MyoD-positive single cells that were also negative for myosin expression and fusion as seen in control cells (data not shown). This inhibition, up to 30%, was proportional to the increased expression of CDK4 in the transfected cells (FIG. 6). Forced nuclear expression of CDK4 inhibits myogenic conversion of 10T1/2 cells in differentiation medium (DM) in the absence of cyclin D1.

Therefore, the expression of CDK4 targeted to the nucleus, in the absence of cyclin D1 expression, can inhibit MyoD function in a concentration dependent manner, as measured by the reduction in the myogenic conversion of 10T1/2 mouse fibroblasts. From this result we conclude that activated CDK4 is not required to inhibit myogenesis since cyclin D1 is not expressed in cells maintained in differentiation medium. Although cyclin D3 expression is upregulated in differentiated muscle cultures, the cytoplasmic location of CDK4 in myotubes suggests that an active cyclin D3-CDK4 nuclear complex is not formed in low mitogen medium. Therefore, we assume the forced nuclear localization of CDK4, in the absence of endogenous cyclin D1, does not form an active kinase with cyclin D3.

VIII. Phosphorylation

In this Example, the inventors examined whether an active CDK4 could phosphorylate MyoD directly to inhibit MyoD transactivation functions, by first examining whether or not MyoD could be phosphorylated by CDK4.

Production of Activated CDK4

Activated CDK4 was prepared from baculovirus infected Sf9 cell extracts essentially as described in Example I.

Phosphorylation

An in vitro kinase assay was performed using activated, immunoprecipitated CDK4 prepared from Sf9 cell extracts. 1–5 µl of Sf9 cell extract was mixed with 10 µl protein-G slurry (1:1 by volume of protein G suspension) washed with kinase buffer (50 mM Hepes, pH 7.5, 10 mM MgCl2, 1 mM DTT) and 1 µl of antibody (Santa Cruz; cat. no. sc-260-G) for one hour on ice. The slurry was then washed three times with 1 ml kinase buffer and then mixed with the 100 ng of either GST-RB target (pRB, amino acids 769–928, Kato et al., *Genes Dev.*, 1993, 7(3): p. 331–342) or renatured his-tagged MyoD plus or minus 200 ng of GST-p16 (Serrano et al., *Nature*, 1993, 336(6456): p. 704–707) incubated in 20 µl of kinase buffer and assayed as described by Kato et al., supra.

Results

RB phosphorylation was sensitive to the CDK4 inhibitor, p16 (FIG. 7, lanes 1 to 3) whereas MyoD phosphorylation was essentially insensitive to p16 inhibition (FIG. 7, lanes 4 and 5) and was considered CDK4-independent. 2D-peptide maps for MyoD, +/−p16, using Glu-C and proteinase K reveal no qualitative differences in the phosphopeptide pattern (data not shown). Phosphorylation inhibited by the addition of p16 to the kinase reaction, a specific CDK4 inhibitor, was assumed to be the CDK4-dependent component of the phosphorylation reaction.

Figure 7:
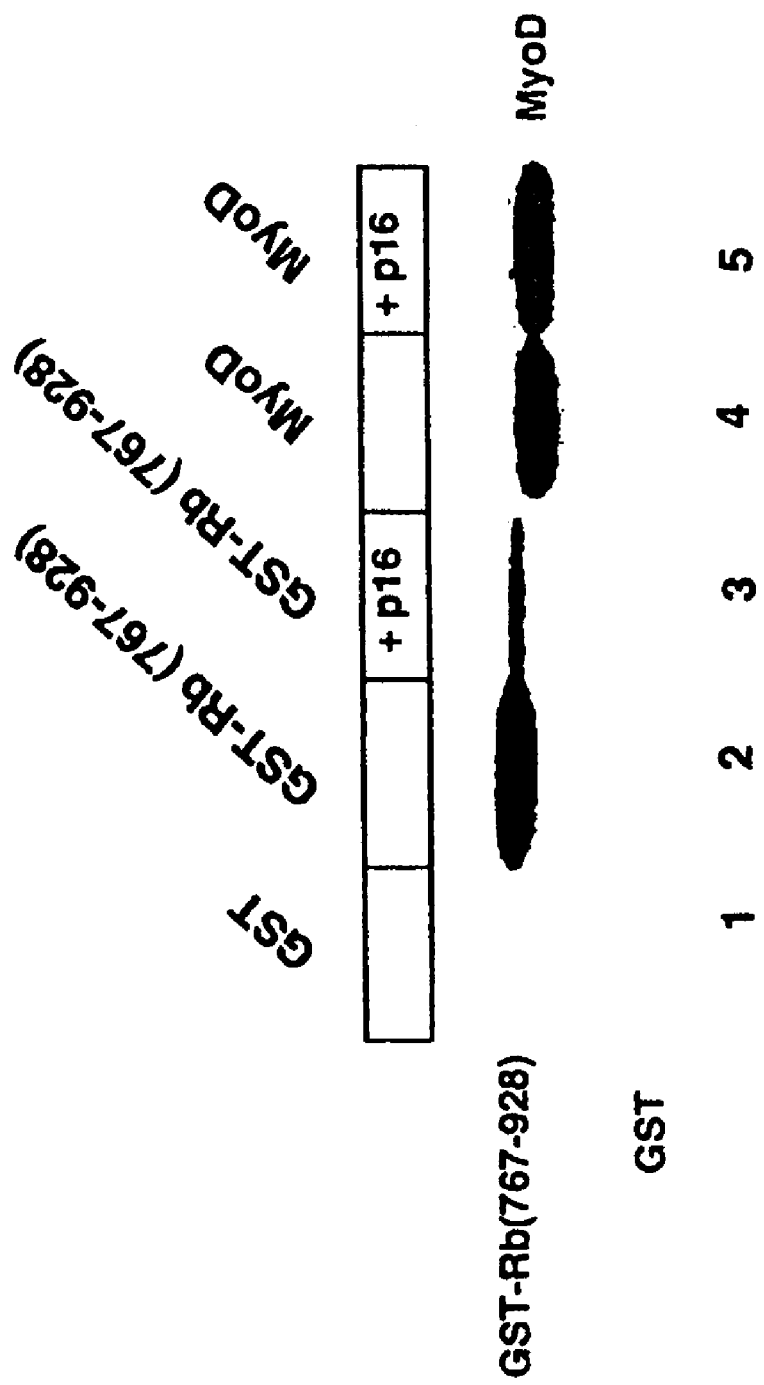
FIG. 7 is a photograph of a gel showing that MyoD and RB are not phosphorylated comparably by CDK4 in vitro.

Of the RB phosphorylation observed, 90–95% was inhibited by p16 (FIG. 7, lanes 2 and 3) whereas only 10–20% of the MyoD phosphorylation was sensitive to p16 in the reaction, as determined by phosphoimager analysis (FIG. 7, lanes 4 and 5). Two-dimensional phosphopeptide maps of MyoD protein, phosphorylated in the presence and absence of p16 and digested either with Glu-C or proteinase K, also demonstrated no qualitative differences in the phosphopeptide patterns for either enzyme (data not shown). We assume that the non-CDK4-type kinases coprecipitated nonspecifically with the CDK4 antibody are responsible for the p16-insensitive MyoD phosphorylation since both p16 and MyoD bound to CDK4 inhibit kinase activity. Our data do not support the hypothesis that cyclin D1 inhibition of myogenesis is associated with a CDK4-dependent phosphorylation of MyoD since CDK4, in the absence of cyclin D1, can block both MyoD DNA-binding and the myogenic conversion of 10T1/2 cells, and MyoD is a very poor substrate for CDK4 phosphorylation in vitro compared to RB.

IX. Mammalian Two-Hybrid System

To determine whether the MyoD-RB reaction is dependent upon the expression levels of MyoD in the cell, the mammalian two-hybrid system was used to analyze MyoD, myogenin and RB interactions in vivo in C2C12 muscle cells under growth and differentiation conditions.

Vector Preparation

Chicken MyoD (CMD1) and myogenin were PCR amplified from pRSET clones (described by Shirakata, et al., *Genes Dev*, (1993), 7(12A): 2456–70) using Pfu polymerase (Stratagene), a 5' primer containing a BamH1 site and a 3' primer with a Hind3 site, and cloned into the corresponding sites in the vp16 vector pVP16 (Clonetech). E2F was cut from CMV-E2F (described by Helin, et al., (1993), *Mol Cell Biol*, 13(10): 6501–8) with BamH1, flush ended with T4 DNA polymerase and cloned into pVP16 that had been cut with Mlu1 and flush ended. Human RB (described by Kaye, et al., (1990), *Proc Natl Acad Sci USA*, 87(17): 6922–6) was cloned as a flush BamH1/Asp718 fragment into the flush Mlu1 site in the gal4 vector pM (Clonetech). Chicken E12 was cloned into the gal4 DNA-binding domain vector, pM. The sequence of chicken E12 is unpublished (Paterson lab). However, it is very similar to the human sequence, which is published, and the human sequence could be used in its place. Myogenin (ch-myogenin), (gene bank accession number D90157) was inserted into the vp16 activation domain plasmid, pVP16.

Cell Culture and Transfection

C2C12 myoblasts ($3\times10^5$ cells per 60 mm dish or multiwell plate) were grown in DMEM with 20% fetal calf serum and transfected with the vectors described above using Fugene-6 (Boehringer Mannheim) according to the manufacturers directions.

1 μg of gal4 luciferase reporter, 2 μg each of the gal4 and vp16 constructs, and 300 ng of beta galactosidase expression plasmid, pCH110 (Pharmacia), for a total of 5.3 μg DNA, was used for each transfection.

Cell Harvest and Assay

24–36 hours after transfection, the cells were placed in 2% horse serum plus insulin (10 μg/ml) to induce differentiation. After an additional 24–48 hours, cells were harvested for the luciferase reporter assay. Luciferase assays were performed using a Promega kit (cat. no. E4030) following the manufacturer's instructions and analyzed on a Victor 1420 multi label counter.

Results

Even in the presence of measurable endogenous levels of RB and E2F, both RB and E2F demonstrated significant interaction in C2C12 cells under growth conditions (10–15 fold activation of the luciferase reporter). Additionally, these proteins demonstrated significant interaction in low serum medium (used to induce muscle cell differentiation) See FIG. 8a, line 7.

Figure 8:
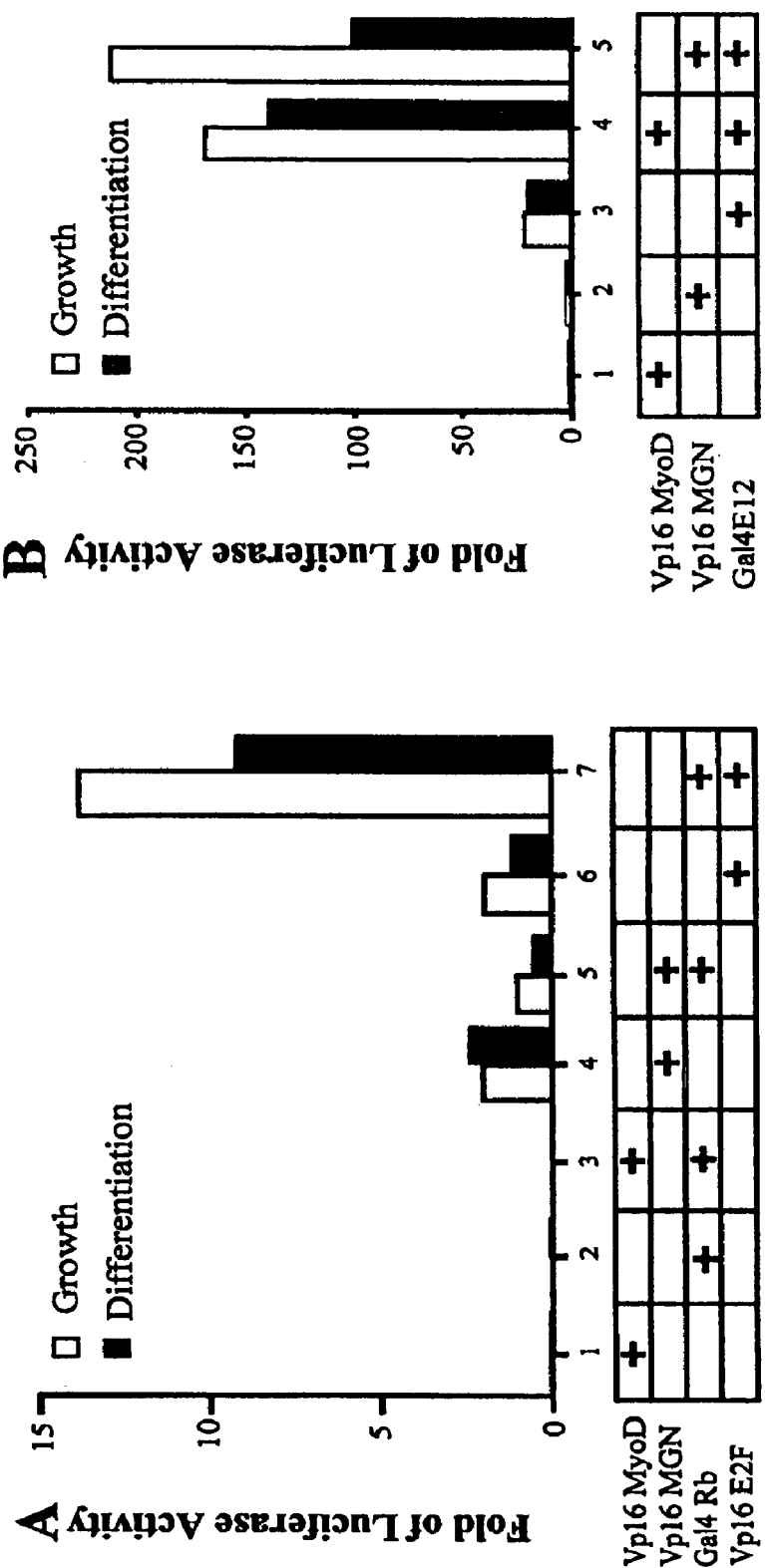
FIG. 8a is a graph showing that gal 4-RB and vp16-E2F interact to activate luciferase expression 10–15 fold routinely, whereas vp16-MyoD and vp16-myogenin show no significant activation above background with gal4-RB.
FIG. 8b is a graph showing that both vp16-MyoD and vp16-myogenin interact strongly with gal4-E12.

In contrast, there was no evidence for any interaction between RB and either MyoD or myogenin (ch-myogenin) in high or low serum culture medium (FIG. 8a, lanes 3 and 5). However, all the control interactions were clearly seen: Both the vp16 MyoD(CMD1) and vp16 myogenin(ch-myogenin) constructs interacted strongly with gal4 E12 (FIG. 8b, lanes 4 and 5), a known partner for these myogenic factors. In addition, both the MyoD and myogenin vp16 constructs were capable of efficiently converting 10T1/2 mouse fibroblasts to muscle (data not shown).

Despite previous reports, these results do not support the hypothesis that either MyoD or myogenin interact with RB to regulate cell cycle decisions in the terminal differentiation of the myoblast. C2C12 cells can differentiate normally under conditions that provide no evidence for an interaction between the myogenic factors and RB.

XI. Mapping the MyoD CDK4 Binding Domain

Preliminary results demonstrated that MyoD binds specifically to CDK4 expressed either in baculovirus infected Sf9 cells or in bacteria, either as a CDK4/cyclin D1 complex or CDK4 alone (data not shown). Thus, the potential MyoD CDK4-binding domain was mapped.

Preparation of MyoD-GST Fusion Proteins

Various domains of MyoD(CMD1), shown in FIG. 9 ($NH_2$, bHLH and COOH fragments) and indicated by amino acid number from chicken MyoD, were amplified by PCR with pPfu with 5' primers containing a BamH1 site and 3' primers with an EcoR1 site and were cloned into the same sites either in pcDNA3 (Invitrogen) or GST-pCEFL (a eukaryotic GST expression vector from S. Gutkind). An NLS (MCPKKRKV) was incorporated into the 5' primer when the amplified fragment did not have a nuclear localization signal.

Fusion Protein Expression

Proteins were expressed in *E. coli* strain BL21 (DE3) and purified as described by Shirakata et al., *Genes Dev.* 1993 7(12A):2456–70. The MyoD-GST fusion proteins were bound to glutathione agaraose.

Binding Experiments

The binding experiments were performed with CDK4 produced in the baculovirus system (Kato et al., *Genes Dev.* 1993 7(3):331–42) essentially as described by Kaelin et al., *Cell* 1991 64(3):521–32.

Deletion Mapping

Figure 10:
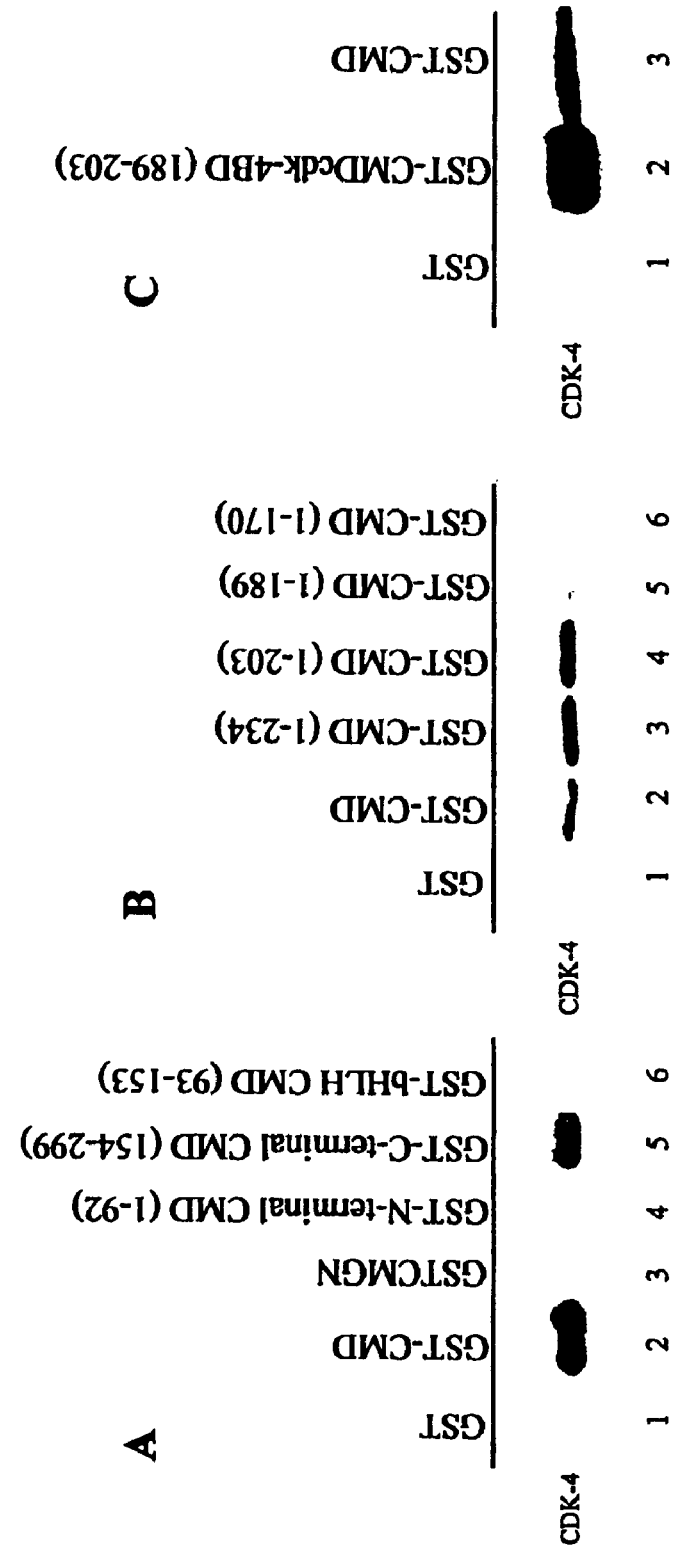
FIG. 10*a* is a photograph of a gel showing that CDK4 binds to the carboxy terminus of MyoD (lane 5) but does not bind to the other vertebrate myogenic factors; GST myogenin shown as an example (lane 3).
FIG. 10*b* is a photograph of a gel showing that a fifteen amino acid domain between amino acid residues 189–203 that is required for CDK4 binding (lanes 4 and 5).
FIG. 10*c* is a photograph of a gel showing that the fifteen amino acid CDK4-binding domain in MyoD (aa 189–203) binds CDK4 as efficiently as full-sized MyoD when joined to GST (lanes 2 and 3).

Deletion mapping of the MyoD (CMD1) carboxy terminus narrowed the CDK4-binding region to a maximum of fifteen amino acids between residues 189–203, well outside the bHLH domain (FIG. 10b, lanes 4 and 5). To confirm that these fifteen amino acids bound CDK4, the fifteen amino acid peptide was joined to glutathione transferase and tested for its ability to bind the CDK4 from Sf9 cell extracts.

Results

Unexpectedly, CDK4 bound to the carboxy terminus of MyoD (CMD1) in the absence of the bHLH domain (FIG. 10a, lane 5). The fifteen amino acid domain in the carboxy terminus of MyoD (CMD1) bound CDK4 as efficiently as full-sized MyoD (CMD1) (FIG. 10c, lanes 2 and 3).

XII. MyoD inhibition of RB

To determine whether MyoD could inhibit CDK4 activity towards RB in addition to the ability of CDK4 to influence MyoD function, MyoD(CMD1) was assayed in a CDK4-dependent phosphorylation reaction for its ability to inhibit the phosphorylation of GST-RB in vitro.

Transfection and Cell Culture

Sf9 cells were infected with wild-type virus, cyclin D1 or CDK4 encoding virus stocks. After incubation for 48 hours at 23° C., cell extracts were made using methods known to those of skill in the art.

Phosphorylation Assay

Extracts produced from Sf9 cells coinfected with virus stocks encoding cyclin D1 and CDK4 were used as a source of activated kinase. Antibody to phosphoserine 780, a CDK4-specific site in RB, was used to measure phosphorylation. Myogenin was used as a control since it does not bind MyoD (FIG. 10a, lane 3). Knudsen, et al., *Cell Biol*, (1997),17(10):5771–83; and Kitagawa, et al., *Embo J*, (1996),15(24):7060–9.

Results

Extracts from Sf9 cells coinfected with wild-type virus (FIG. 11a, lane 1), a cyclin D1 encoding virus (FIG. 11a, lane 2) or a CDK4 encoding virus (FIG. 11, lane 3) give background levels of kinase activity on serine 780 (antibody to phosphoserine 780). Coinfections with baculovirus stocks encoding CDK4 and cyclin D1 produce active CDK4 (FIG. 11a, lane 4) that specifically phosphorylates RB (GST-RB (aa 767–928)) on serine 780. Phosphorylation is inhibited to background levels (e.g., by more than 90%) by the CDK4-specific kinase inhibitor, p16 (FIG. 11a, lane 5, added as GST-p16).

XIII. Demonstration of CDK4 Binding Peptide Inhibitory Properties

In this experiment, both the full-sized and the carboxy terminal domain of MyoD (CMD1), were titrated in the CDK4-dependent phosphorylation reaction to test their ability to inhibit kinase activity. Myogenin, which does not bind to CDK4, was used as the control. As before, CDK4-dependent phosphorylation of RB was measured using an antibody to phosphoserine 780.

As used herein, the term "amino terminus of MyoD" refers to amino acids 1–92 of CMD1. The "bHLH domain" refers to amino acids 93–153. The "carboxy terminus" refers to amino acids 153–298. The "fifteen amino acid CDK4-binding peptide" refers to amino acids 189–203. Amino acid 299 is a terminator codon.

Transfection and Cell Culture

Active CDK4 was produced in Sf9 cells coinfected with baculovirus stocks encoding CDK4 and cyclin D1 (from C. J. Sherr).

A. CDK4 Kinase Assay

The kinase assay was performed essentially as described by Kato, et al., *Genes Dev*, (1993), 7(3):331–42. The CDK4-specific kinase inhibitor p16 (from D. Beach, [as described in Serrano, et al., *Nature*, (1993), 366(6456): 704–7]) was used as a GST-p16 fusion added to the kinase reaction. The GST-RB fusion (767–928) was used as a kinase target as previously described Kato, et al., *Genes Dev*, (1993), 7(3): 331–42.

To test for kinase inhibition, the various proteins and protein domains were added to the reaction in two-fold increments from 75 ng to 300 ng. For the pCDNA3 constructs, total protein concentration was kept constant in the kinase reaction by adding a 6-his tagged amino terminus of MyoD (CMD1) (aa 1–92), which does not bind CDK4. For the GST constructs, total protein concentration was kept constant in the kinase reaction by adding GST protein. After the assay the total reaction was run on SDS PAGE gels and analyzed by Western blot analysis. Specific phosphorylation of RB was measured with rabbit polyclonal antibodies to RB phosphoserines 780 or 795 (New England Biolabs).

Results

As shown in FIG. 11b, full-length MyoD(CMD1) (second row), the C-terminus of MyoD(CMD1) (third row) and the fifteen amino acid CDK4-binding peptide fused to GST (fourth row) inhibit the CDK4-dependent phosphorylation of RB(GST-RB) in vitro. Myogenin (first row) (ch-myogenin), which does not bind to CDK4, had no inhibitory effect (FIG. 11b, top row). Similarly, neither the N-terminus (amino acids 1–92) nor the bHLH domain of MyoD(CMD1) inhibited CDK4 activity (data not shown). GST protein alone was not inhibitory and behaved similar to myogenin (data not shown). Identical results were obtained using an antibody to phosphoserine 795, another CDK4 dependent phosphorylated residue in RB (data not shown).

Therefore, the observed MyoD-CDK4 interaction in vitro can specifically inhibit the phosphorylation of RB in a dose-dependent manner on serine residues known to be targeted by CDK4. Thus, forced expression of either MyoD or its CDK4-binding subdomain should inhibit CDK4 in cells to block the phosphorylation of RB and arrest growth, similar to the growth inhibitory effects of full-length MyoD.

B. BrdU Incorporation Assay

A BrdU incorporation assay was employed to determine whether expression of either the carboxy terminus or the minimal fifteen amino acid CDK4-binding domain of MyoD (CMD1) could induce growth arrest in cultured cells.

Transfection & Cell Culture

10T1/2 cells in growth medium were cotransfected with plasmids expressing full-sized MyoD(CMD1) or the indicated domains, either as GST fusions in GST-pCEFL or as subclones in pCDNA3, along with a lacZ expression construct, pCH110, to mark transfected cells. The various domains were targeted to the nucleus with a nuclear tag in the absence of an existing NLS.

BrdU Assay

Cultures were maintained in 20% fetal calf serum. 72 hours after transfection cultures were refed with the same medium and 12 hours later they were given a one hour pulse with BrdU (10 µM) prior to fixation, as previously described by Crescenzi et al., PNAS USA 1990 87(21):8442–6; and Sorrentino et al., Nature, 1990 345(6278):813–5. Cells were then reacted with rabbit anti-BrdU antibody (Jackson labs) and Xgal.

Results

A typical result used in the scoring assay (Sorrentino et al., *Nature,* 1990, 345(6278): p. 261–72 and Crescenzi et al., *Proc. Natl. Acad. Sci. USA,* 1990, 87(21): p. 8442–6) to measure the percentage of BrdU positive cells with the transfected cells expressing the various domains of MyoD labeled cells (indicating the cotransfected beta galactosidase expression vector) is shown. All the GST-MyoD domain constructs used were localized to the nuclei of transfected cells, as typified for the fifteen amino acid CDK4-binding peptide fusion with an NLS. Neither the empty vectors (pCDNA3 or GST-pCEFL with an NLS) nor the amino terminal portion of MyoD(CMD1) (amino acids 1–92 in pCDNA3 with an NLS) were able to inhibit cell growth (FIG. 12). In contrast, full MyoD(CMD1) showed growth inhibitory activity (FIG. 12).

The amino terminus of MyoD(CMD1) (amino acids 1–92) was ineffective in growth inhibition whereas the bHLH domain (amino acids 93–153) and, to an even greater extent, the carboxy terminus (amino acids 153–298) were both effective at inhibiting cell growth (FIG. 12, upper section). Again, the fifteen amino acid CDK4-binding peptide from the carboxy terminus (amino acids 189–203) was as potent as full-sized MyoD(CMD1) in growth inhibitory activity in this assay (FIG. 12, lower section). The bHLH domain of MyoD alone also triggered growth arrest, although to a lesser extent.

C. Phosphorylation of RB

This experiment is designed to confirm that growth arrest correlates with a change in the phosphorylation status of RB induced by MyoD.

Vector Preparation

The inhibitory activity of the fifteen amino acid CDK4 binding peptide on RB phosphorylation in cells was examined by fusing the fifteen amino acid CDK4-binding peptide of MyoD with a nuclear localization tag to the carboxy terminus of GFP and used in the same transfection protocol with GST-RB.

Transfection and Cell Culture

10T1/2 cells were cotransfected with a GST-RB target (amino acids 767–928) containing a nuclear localization tag, and either MyoD(CMD1) or the carboxy terminus of MyoD with an NLS.

Recovery of GST-RB 48 hours after transfection, nuclear extracts of the 10T1/2 cells were prepared. The nuclear extracts were passed over glutathione agaraose to capture the GST-RB target.

Western Blotting

Western blot analysis of the captured GST-RB target was performed with phosphoserine specific antibodies to the CDK4 target sites, serines 780 and 795. Gel loadings for the phosphoserine antibody analysis were adjusted to the same amount of GST-RB target protein by preliminary western analysis of the extracts (FIG. 13).

Results

Figure 13:
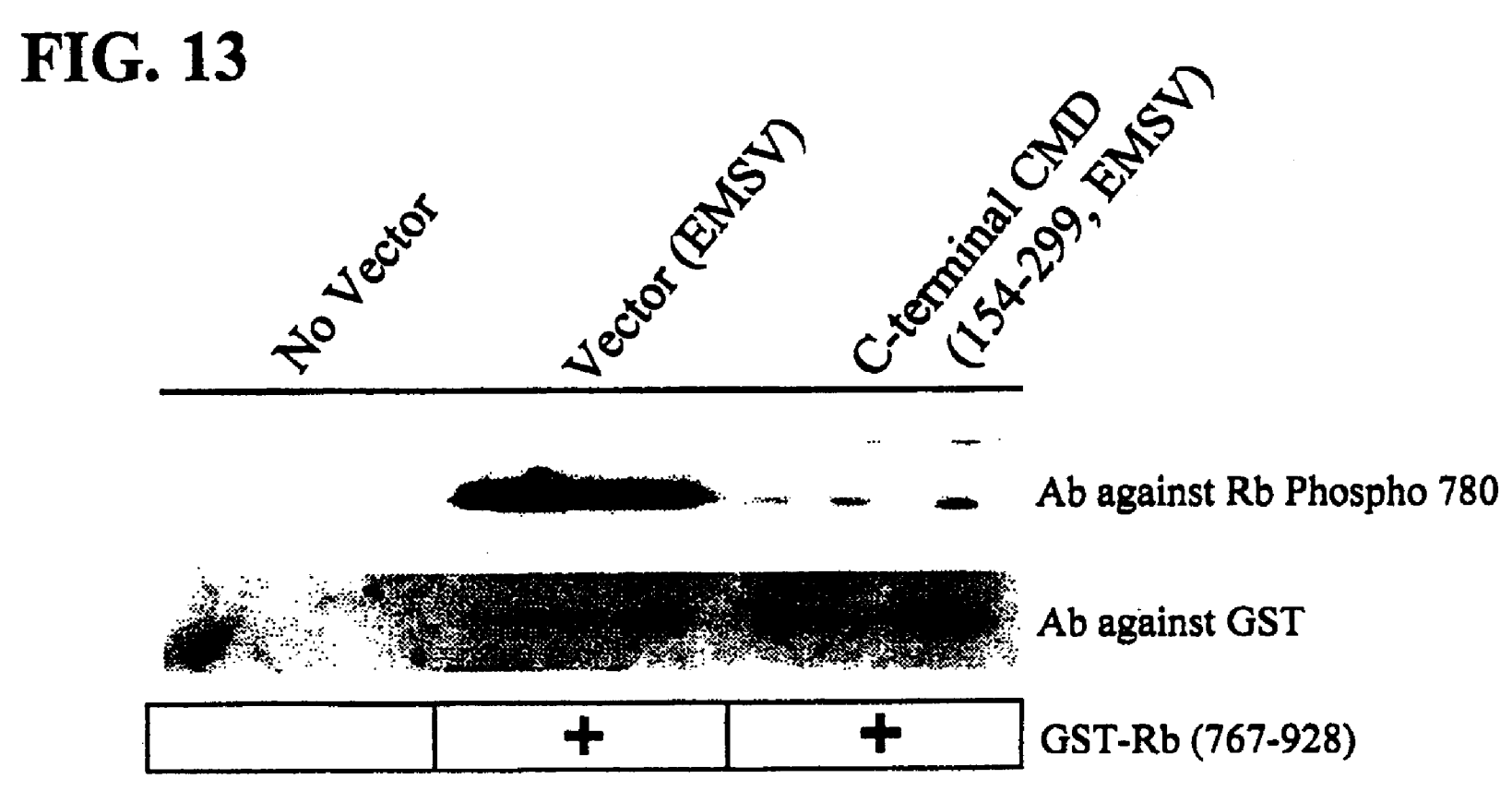

Both the full sized and the carboxy terminal domain of MyoD (CMD1) reduced the phosphorylation of serines 780 and 795 on the cotransfected RB target protein, as shown for the C-terminus with antibodies to phosphoserines 780 and 795 (FIG. 13)

D. Growth Inhibition

This experiment was designed to test the inhibitory activity of the fifteen amino acid CDK4-binding peptide on RB phosphorylation in cells.

Transfection

C2C12 myoblasts were cotransfected with a GST-pCEFL RB expression plasmid (RB aa 767–928) and pCDNA3 expression plasmids for full-sized or the C-terminus of MyoD(CMD1). GST-RB was recovered from the cells using methods known to those of skill in the art. The samples were adjusted for equal levels GST protein and loaded on SDS-PAGE gels for western analysis by phosphoserine 780 and 795-specific antibodies.

Results

The 15 amino acid domain in the carboxy terminus of MyoD that binds CDK4 also inhibits CDK4 kinase activity and cell growth when expressed in cell nuclei.

The entire disclosures of all citations cited throughout the specification, and the references cited therein, are hereby expressly incorporated by reference.

Although the foregoing refers to particular preferred embodiments, it will be understood that the present invention is not so limited. It will occur to those ordinarily skilled in the art that various modifications may be made to the disclosed embodiments without diverting from the overall concept of the invention. All such modifications are intended to be within the scope of the present invention. Thus only such limitations as appear in the appended claims should be placed upon the scope of the present invention.

What is claimed is:

1. An isolated peptide comprising:

Tyr-Ser-Gly-Pro-Pro-Ser-Gly-Ala-Arg-Arg-Arg-Asn-Cys-Tyr-Glu (SEQ ID NO:1);

wherein the isolated peptide does not include a basic helix-loop-helix (bHLH) domain;

wherein the isolated peptide binds cyclin dependent kinase 4.

2. A fusion protein comprising:

(a) a peptide comprising Tyr-Ser-Gly-Pro-Pro-Ser-Gly-Ala-Arg-Arg-Arg-Asn-Cys-Tyr-Glu (SEQ ID NO:1), wherein the peptide binds cyclin dependent kinase 4; and (b) a heterologous amino acid sequence.

3. The fusion protein of claim 2 wherein the heterologous amino acid sequence comprises a nuclear localization signal.

4. The fusion protein of claim 3 wherein the peptide is at the C-terminus of the fusion protein.

5. A method of inhibiting the activity of CDK4 comprising:

contacting CDK4 with a CDK4 binding peptide comprising:

Tyr-Ser-Gly-Pro-Ser-Gly-Ala-Arg-Arg-Asn-Cys-Tyr-Glu (SEQ ID NO:1), wherein the peptide does not include a basic helix-loop-helix domain in an amount effective to inhibit the activity of CDK4.

* * * * *

SEQUENCE LISTING

```
<160> NUMBER OF SEQ ID NOS: 9

<210> SEQ ID NO 1
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa is an amino acid having an uncharged polar
      side chain, including Cys or Ser
<220> FEATURE:
<221> NAME/KEY: MISC_FEATURE
<222> LOCATION: (7)..(7)
<223> OTHER INFORMATION: Xaa is an amino acid having an uncharged side
      chain, including Ser or Gly
<220> FEATURE:
<221> NAME/KEY: MISC_FEATURE
<222> LOCATION: (8)..(8)
<223> OTHER INFORMATION: Xaa is an amino acid having an uncharged side
      chain, including Ser, Ala or Pro
<220> FEATURE:
<221> NAME/KEY: MISC_FEATURE
<222> LOCATION: (11)..(11)
<223> OTHER INFORMATION: Xaa is an amino acid having a polar side chain,
      including Arg or Gln
<220> FEATURE:
<221> NAME/KEY: MISC_FEATURE
```

```
<222> LOCATION: (13)..(13)
<223> OTHER INFORMATION: Xaa is an amino acid having an uncharged side
      chain, including Ser, Cys or Gly
<220> FEATURE:
<221> NAME/KEY: MISC_FEATURE
<222> LOCATION: (15)..(15)
<223> OTHER INFORMATION: Xaa is an amino acid having a charged polar
      side chain, including Asp or Glu

<400> SEQUENCE: 1

Tyr Ser Gly Pro Pro Xaa Xaa Xaa Arg Arg Xaa Asn Xaa Tyr Xaa
1               5                   10                  15

<210> SEQ ID NO 2
<211> LENGTH: 16
<212> TYPE: PRT
<213> ORGANISM: Gallus gallus

<400> SEQUENCE: 2

Tyr Ser Gly Pro Pro Cys Ser Ser Arg Arg Arg Asn Ser Tyr Asp Ser
1               5                   10                  15

<210> SEQ ID NO 3
<211> LENGTH: 16
<212> TYPE: PRT
<213> ORGANISM: Homo sapiens

<400> SEQUENCE: 3

Tyr Ser Gly Pro Pro Ser Gly Ala Arg Arg Arg Asn Cys Tyr Glu Gly
1               5                   10                  15

<210> SEQ ID NO 4
<211> LENGTH: 16
<212> TYPE: PRT
<213> ORGANISM: Rattus rattus

<400> SEQUENCE: 4

Tyr Ser Gly Pro Pro Ser Gly Pro Arg Arg Gln Asn Gly Tyr Asp Ala
1               5                   10                  15

<210> SEQ ID NO 5
<211> LENGTH: 16
<212> TYPE: PRT
<213> ORGANISM: Mus musculus

<400> SEQUENCE: 5

Tyr Ser Gly Pro Pro Ser Gly Pro Arg Arg Gln Asn Gly Tyr Asp Thr
1               5                   10                  15

<210> SEQ ID NO 6
<211> LENGTH: 16
<212> TYPE: PRT
<213> ORGANISM: Sus scrofa

<400> SEQUENCE: 6

Tyr Ser Gly Pro Pro Ser Gly Ala Arg Arg Arg Asn Cys Tyr Asp Gly
1               5                   10                  15

<210> SEQ ID NO 7
<211> LENGTH: 15
<212> TYPE: PRT
<213> ORGANISM: Xenopus laevis

<400> SEQUENCE: 7

Tyr Asn Ser Pro Pro Cys Gly Ser Arg Arg Arg Asn Ser Tyr Asp
1               5                   10                  15
```

```
<210> SEQ ID NO 8
<211> LENGTH: 15
<212> TYPE: PRT
<213> ORGANISM: Xenopus laevis

<400> SEQUENCE: 8

Tyr Asn Ser Pro Pro Cys Ser Ser Arg Arg Arg Asn Ser Tyr Asp
1               5                   10                  15

<210> SEQ ID NO 9
<211> LENGTH: 15
<212> TYPE: PRT
<213> ORGANISM: Brachydanio rerio

<400> SEQUENCE: 9

Phe Met Gly Pro Thr Cys Gln Thr Arg Arg Arg Asn Ser Tyr Asp
1               5                   10                  15
```